United States Patent
Kline et al.

(10) Patent No.: US 7,828,741 B2
(45) Date of Patent: Nov. 9, 2010

(54) UTILIZING LIPOPOLYSACCHARIDE IN EXHALED BREATH CONDENSATE TO DIAGNOSE GRAM NEGATIVE PNEUMONIA

(75) Inventors: Jeffrey A. Kline, Charlotte, NC (US); Jackeline Hernandez, Charlotte, NC (US); John Albert Watts, Jr., Huntersville, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 915 days.

(21) Appl. No.: 11/135,265

(22) Filed: May 23, 2005

(65) Prior Publication Data

US 2005/0208614 A1 Sep. 22, 2005

Related U.S. Application Data

(63) Continuation-in-part of application No. 10/742,721, filed on Dec. 19, 2003, which is a continuation-in-part of application No. 10/778,477, filed on Feb. 13, 2004, now Pat. No. 7,547,285.

(60) Provisional application No. 60/577,641, filed on Jun. 7, 2004, provisional application No. 60/447,581, filed on Feb. 14, 2003, provisional application No. 60/434,916, filed on Dec. 20, 2002.

(51) Int. Cl.
*A61B 5/08* (2006.01)
(52) U.S. Cl. .................. 600/532; 600/529
(58) Field of Classification Search ................. 436/900; 600/532
See application file for complete search history.

(56) References Cited

U.S. PATENT DOCUMENTS

| | | | |
|---|---|---|---|
| 3,000,379 A | 9/1961 | Viers | 121/191 |
| 3,420,224 A | 1/1969 | Farr | 128/2.07 |
| 3,509,771 A | 5/1970 | Moberg et al. | 73/421.5 |
| 3,613,665 A | 10/1971 | Gorsuch | 128/2 R |
| 3,622,278 A | 11/1971 | Elzinga et al. | 23/232 R |
| 3,830,630 A | 8/1974 | Kiefer et al. | 23/232 E |
| 4,248,245 A | 2/1981 | Kempin | 128/719 |
| 4,259,951 A | 4/1981 | Chernack et al. | 128/200.14 |
| 4,322,217 A | 3/1982 | Dikeman | 23/230 |
| 4,349,626 A | 9/1982 | Labows et al. | 435/38 |

(Continued)

FOREIGN PATENT DOCUMENTS

EP 0 759 169 B1 2/1997

(Continued)

OTHER PUBLICATIONS

Luna et al. "Impact of BAL Data on the Therapy and Outcome of Ventilator-Associated Pneumonia" Chest 1997; 111; 676-685. accessed at http://chestjournal.org/cgi/content/abstract/111/3/676.*

(Continued)

*Primary Examiner*—Patricia C Mallari
(74) *Attorney, Agent, or Firm*—K&L Gates LLP

(57) ABSTRACT

A method for determining whether a subject has Gram negative bacterial pneumonia based on the presence of lipopolysaccharide in exhaled breath condensate collected from the subject. The collection devices utilized to collect exhaled breath condensate from both spontaneously breathing and mechanically ventilated subjects and the devices utilized to determine whether lipopolysaccharide is present in the collected exhaled breath condensate.

4 Claims, 14 Drawing Sheets

U.S. PATENT DOCUMENTS

| | | | |
|---|---|---|---|
| 4,370,413 A | 1/1983 | Neeman et al. | 435/39 |
| 4,438,209 A | 3/1984 | Mosier | 436/542 |
| 4,491,660 A * | 1/1985 | Gendrich et al. | 536/32 |
| 4,510,241 A | 4/1985 | Mills | 435/23 |
| 4,717,658 A * | 1/1988 | Michaels | 435/18 |
| 4,818,489 A | 4/1989 | Gönner et al. | 422/84 |
| 4,870,158 A * | 9/1989 | Karol et al. | 530/319 |
| 5,042,501 A | 8/1991 | Kenny et al. | 128/719 |
| 5,186,242 A | 2/1993 | Adachi et al. | 165/110 |
| 5,198,339 A * | 3/1993 | Hansen et al. | 435/7.2 |
| 5,285,794 A | 2/1994 | Lynch | 128/719 |
| 5,310,657 A | 5/1994 | Berzofsky | 435/34 |
| 5,327,901 A | 7/1994 | Delente | 128/730 |
| 5,356,778 A | 10/1994 | Hansen et al. | 435/7.2 |
| 5,376,555 A | 12/1994 | Forrester et al. | 436/132 |
| 5,380,295 A | 1/1995 | Vacca | 604/187 |
| 5,383,469 A | 1/1995 | Vreman et al. | 128/719 |
| 5,465,728 A | 11/1995 | Phillips | 128/730 |
| 5,479,815 A | 1/1996 | White et al. | 73/23.3 |
| 5,487,380 A | 1/1996 | Grabenkort | 128/204.15 |
| 5,501,212 A | 3/1996 | Psaros | 128/205.12 |
| 5,541,057 A | 7/1996 | Bogart et al. | 435/5 |
| 5,558,087 A | 9/1996 | Psaros et al. | 128/205.12 |
| 5,634,517 A | 6/1997 | Linden et al. | 165/111 |
| 5,655,526 A | 8/1997 | Gibertoni | 128/205.27 |
| 5,702,882 A | 12/1997 | Tamura et al. | 435/4 |
| 5,759,858 A | 6/1998 | Nieuwenhuizen | 436/16 |
| 5,787,885 A | 8/1998 | Lemelson | 128/632 |
| 5,795,787 A | 8/1998 | Silkoff et al. | 436/116 |
| 5,826,575 A | 10/1998 | Lall | 128/205.12 |
| 5,876,947 A | 3/1999 | Kudryk et al. | 435/7.1 |
| 5,938,637 A | 8/1999 | Austin et al. | 604/72 |
| 5,998,389 A | 12/1999 | Loverock | 514/54 |
| 6,010,459 A | 1/2000 | Silkoff et al. | 600/532 |
| 6,033,368 A | 3/2000 | Gaston, IV et al. | 600/532 |
| 6,106,783 A * | 8/2000 | Gamble | 422/102 |
| 6,132,610 A | 10/2000 | Hirai et al. | 210/264 |
| 6,148,657 A | 11/2000 | Satoh et al. | 73/23.35 |
| 6,149,603 A | 11/2000 | Parker | 600/532 |
| 6,186,958 B1 | 2/2001 | Katzman et al. | 600/532 |
| 6,221,026 B1 | 4/2001 | Phillips | 600/532 |
| 6,244,096 B1 | 6/2001 | Lewis et al. | 73/23.2 |
| 6,283,122 B1 | 9/2001 | Adahan | 128/205.24 |
| 6,312,390 B1 | 11/2001 | Phillips | 600/532 |
| 6,341,520 B1 | 1/2002 | Satoh et al. | 73/23.35 |
| 6,363,772 B1 | 4/2002 | Berry | 73/24.02 |
| 6,384,188 B1 | 5/2002 | Hoess et al. | 530/526 |
| 6,419,634 B1 | 7/2002 | Gaston, IV et al. | 600/532 |
| 6,491,643 B2 | 12/2002 | Katzman et al. | 600/532 |
| 6,582,376 B2 | 6/2003 | Baghdassarian | 600/543 |
| 6,585,661 B1 | 7/2003 | Hunt et al. | 600/532 |
| 6,612,306 B1 | 9/2003 | Mault | 128/204.22 |
| 6,645,724 B1 | 11/2003 | Ding et al. | 435/7.1 |
| 6,656,127 B1 | 12/2003 | Ben-Oren et al. | 600/532 |
| 6,660,852 B1 * | 12/2003 | Keshi et al. | 536/24.32 |
| 6,726,637 B2 | 4/2004 | Phillips | 600/543 |
| 6,824,520 B2 | 11/2004 | Orr et al. | 600/529 |
| 7,118,537 B2 | 10/2006 | Baddour | 600/543 |
| 2001/0021815 A1 | 9/2001 | Katzman et al. | 600/532 |
| 2003/0050567 A1 | 3/2003 | Baghdassarian | 600/532 |
| 2003/0208132 A1* | 11/2003 | Baddour | 600/532 |
| 2004/0138577 A1 | 7/2004 | Kline | 600/543 |
| 2004/0162500 A1 | 8/2004 | Kline | 600/532 |
| 2004/0234971 A1 | 11/2004 | Jackman | 435/6 |
| 2005/0196868 A1 | 9/2005 | Kline | |
| 2007/0073183 A1 | 3/2007 | Kline | |
| 2007/0100250 A1 | 5/2007 | Kline | |
| 2007/0203424 A1 | 8/2007 | Kline | |

FOREIGN PATENT DOCUMENTS

| | | |
|---|---|---|
| WO | WO 01/84112 A1 | 11/2001 |
| WO | WO 02/082977 A2 | 10/2002 |
| WO | WO 2004/058125 A2 | 7/2004 |
| WO | WO 2005/085870 A1 | 9/2005 |
| WO | WO 2006/007180 A2 | 1/2006 |
| WO | WO 2006/127704 A2 | 11/2006 |

OTHER PUBLICATIONS

Lindsay et al. "Single-Step, Chromogenic Limulus Amebocyet Lysate Assay for Endotoxin". Journal of Clinical Microbiology, May 1989, pp. 947-951.*

Moloney et al. "Exhaled Breath Condensate Detects Markers of Pulmonary Inflammation after Cardiothoracic Surgery". American Journal of Respiratory and Critical Care Medicine, vol. 169, pp. 64-69, 2004.*

Flanagan et al. "Diagnosis of Gram negative, ventilator associated pneumonia by assaying endotoxin in bronchial lavage fluid". J Clin Pathol 2001; 54: 107-110.*

McCaig, L. and Burt, C.; "National Hospital Ambulatory Medical Care Survey: 2002 Emergency Department Summary"; Advance Data From Vital and Health Statistics, No. 340, Mar. 18, 2004, pp. 1-35.

Kollef, M.H. and Eisenberg, P.R., "A Rapid Qualitative Assay to Detect Circulating Endotoxin Can Predict the Development of Multiorgan Dysfunction"; Chest, vol. 112, 173-180, © by American College of Chest Physicians, 1997.

Schreiber, J.; Meyer C.; Rüsch-Gerdes, S., Richter, E.; Beck, H.; Fischer; and J.F., Rosahl, W.; "*Mycobacterium tuberculosis* Gene-Amplification in Breath Condensate of Patients With Lung Tuberculosis"; Eur J Med Res (2002) 7:290-291.

Vogelberg, C., Hirsch, T., Rösen-Wolff, A., Kerkmann, M. and Leupold, W., "*Pseudomonas aeruginosa* and *Burkholderia cepacia* Cannot Be Detected by PCR in the Breath Condensate of Patients With Cystic Fibrosis"; Pediatric Pulmonology 36:348-352 (2003).

Flanagan, P.G., Jackson, S. K., Findlay, G., "Diagnosis of Gram negative, ventilator associated pneumonia by assaying endotoxin in bronchial lavage fluid", *J. Clin. Pathol.* 2001, 54:107-110.

Pugin, J.; Auckenthaler R.; Delaspre, O.; VanGessel, E.; Suter, P.; "Rapid Diagnosis of Gram-negative pneumonia by assay of endotoxin in bronchoalveolar lavage fluid", *Thorax*. 1992, 47:547-549.

International Search Report, PCT/US04/04321, International Filing Date Feb. 13, 2004.

International Search Report, PCT/US05/18232, International Filing Date May 24, 2005.

*Untersuchungen zur Anwendbarkeit der Atemkondensatgewinnung beim Pferd und ihre Potentiellen Einsatzmöglichkeiten in der Lungendiagnostik*, Sandra Schack, Abstract, http://bibd.uni-giessen.de/ghtm/2002/uni/d020068b.htm, Nov. 19, 2002, 1 page.

*Total Nitrite/Nitrate in Expired Breath Condensate of Patients With Asthma*, K. Ganas et al., Pneumon, http://www.mednet.gr/pneumon/1403-6e.htm, Nov. 19, 2002, 1 page.

*Breath Condensate: Rich Source of Exhaled Markers and Mediators. Methodological Issues and Standardisation of Measurements*, Kharitonov et al., National Heart and Lung Institute, Imperial College, Dovehouse Street, London SW3 6LY, UK, www.filt.de/Hauptmenue/Aktuelles_Current_Affairs/Page10464/Breath/_Condensate, Nov. 19, 2002, 2 pages.

*Expired Hydrogen Peroxide in Breath Condensate of Cystic Fibrosis Patients*, L.P. Ho et al., Abstract, Eur Respir J 1999; 13:103-106, http://www.personal.u-net.com/ , Nov. 19, 2002.

*Meeting Report—World Congress on Lung Health and 10th ERS Annual Congress* Aug. 30-Sep. 3, 2000, Florence, Italy, Pieter S. Hiemstra, Respir Res 2000, 1:178-179, http://respiratory-research.com/content/1/3/178.

*Breath Condensate*, info Special Edition, 1st Edition, Apr. 2001, JAEGER a subsidiary of VIASYS Healthcare, Hoechberg, Germany, pp. 1-28.

Sergei A. Kharitonov and Peter J. Barnes, "Exhaled Markers of Pulmonary Disease", *American Journal of Respiratory and Critical Care Medicine*, vol. 163, pp. 1693-1722, 2001.

George Nakos, Eirene I. Kitsiouli and Marilena E. Lekka, "Bronchoalveolar Lavage Alterations in Pulmonary Embolism", *American Journal of Respiratory and Critical Care Medicine*, vol. 158, pp. 1504-1510, 1998.

Matthias Griese, Jochen Noss, Christina von Bredow, "Protein Pattern of Exhaled Breath Condensate and Saliva", *Proteomics* 2002, 2, pp. 690-696.

Zlotnik and Yoshie, "Chemokines: A New Classification System and Their Role in Immunity," *Immunity*, 2000, 12:121-127.

Kimura et al. "Alleviation of Monocrotaline-Induced Pulmonary Hypertension by Antibodies to Monocyte Chemotactic and Activating Factor/Monocyte Chemoattractant Protein-1," *Laboratory Investigation* 1998 78:571-81.

Ikeda et al.,"Anti-monocyte chemoattractant protein-1 gene therapy attenuates pulmonary hypertension in rats," *Am J Physiol Heart Circ Physiol*, 2002, 283(5):H2028.

Supplemental European Search Report.

U.S. Appl. No. 10/884,179, filed Jul. 3, 2004, Kline.

European Search Report.

F. Nyeri, et al., "Exhaled breath condensate and serum levels of hepatocyte growth factor in pneumonia", *Respiratory Medicine*, vol. 96 (Dec. 10, 2002) p. 115-119, Bailliere Tindall, London, GB.

\* cited by examiner

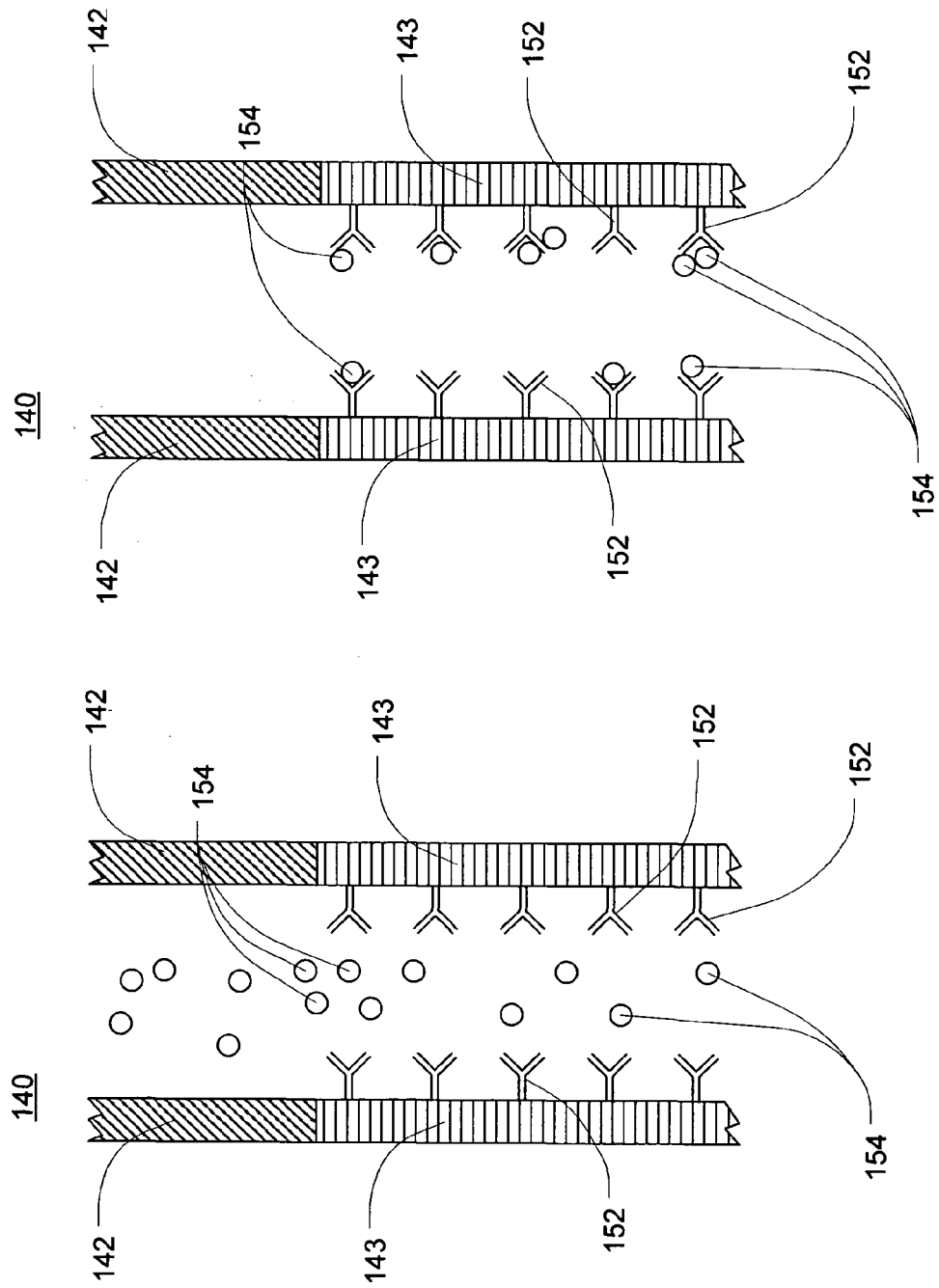

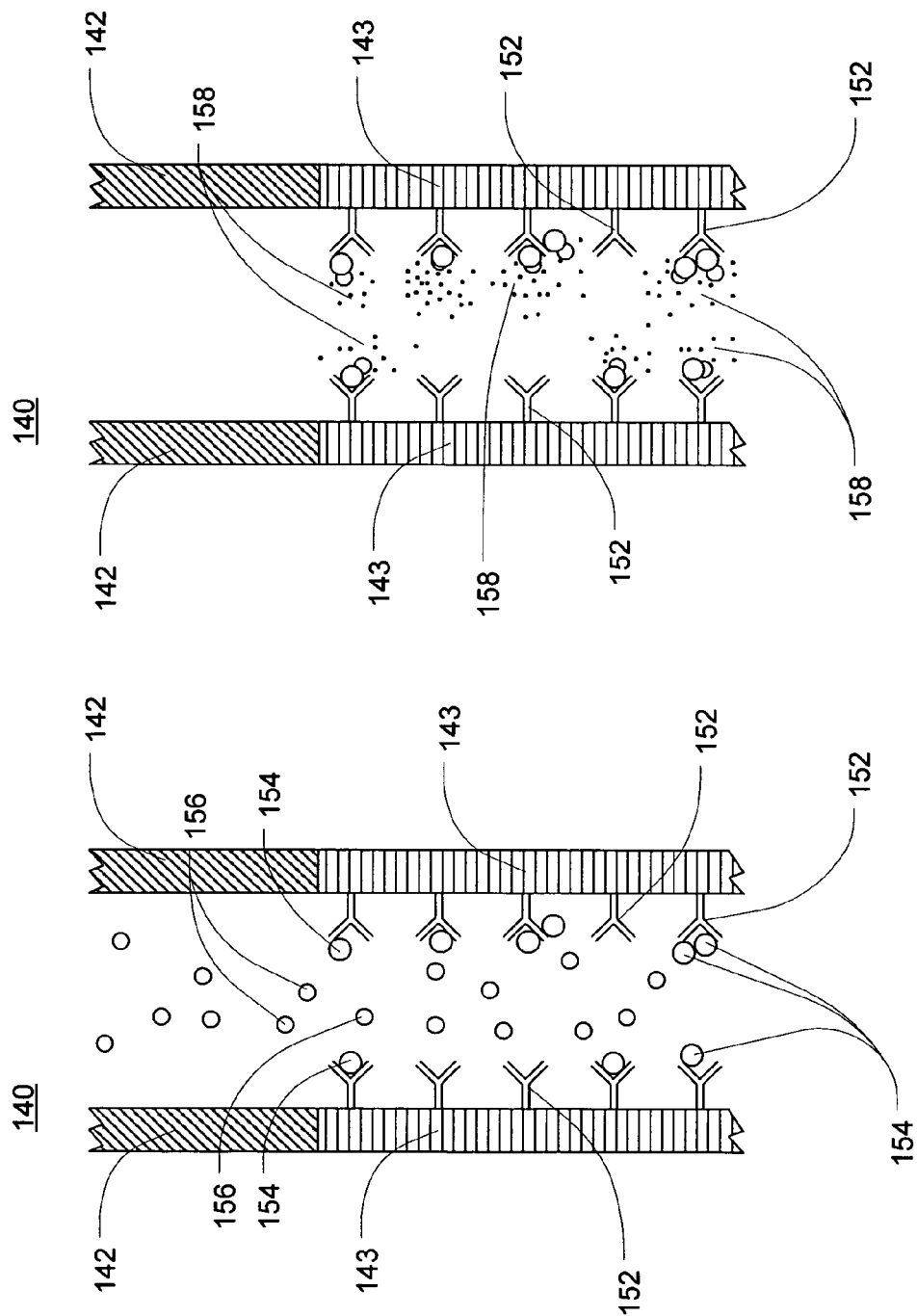

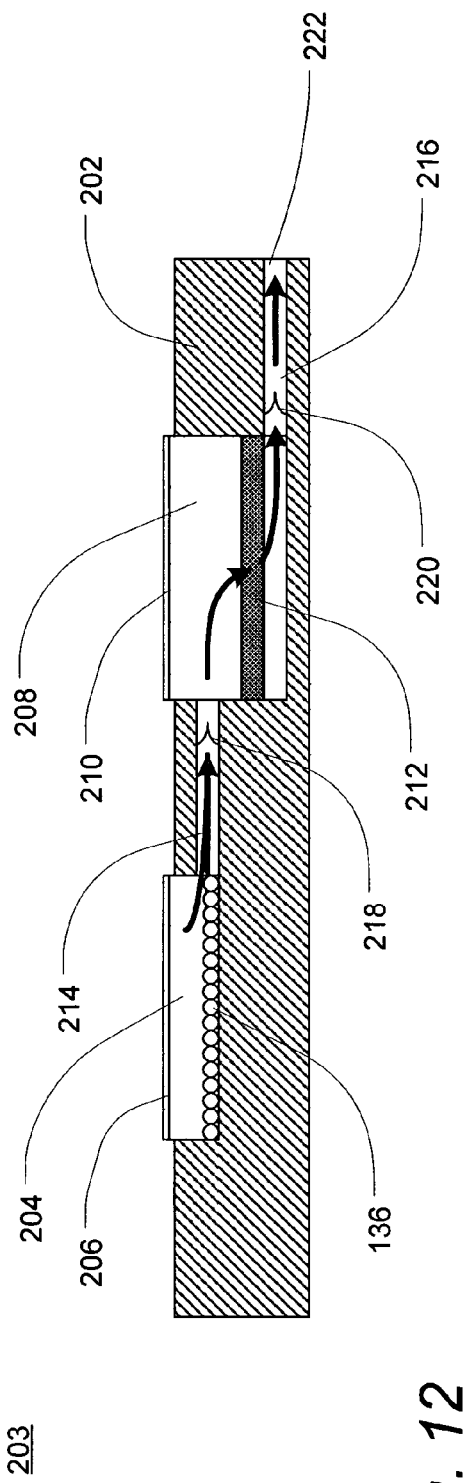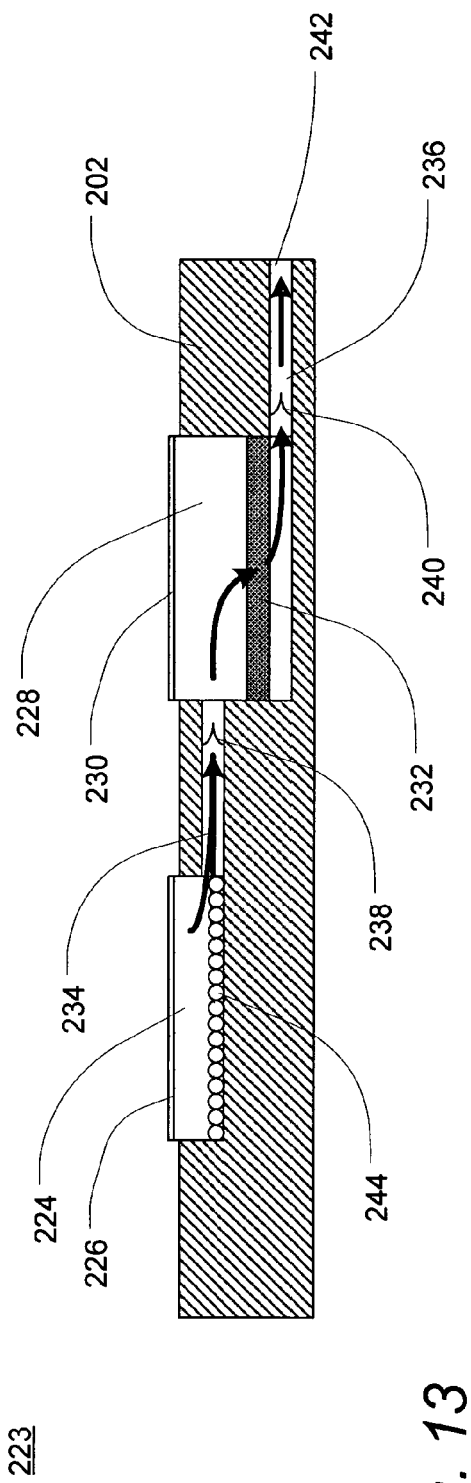

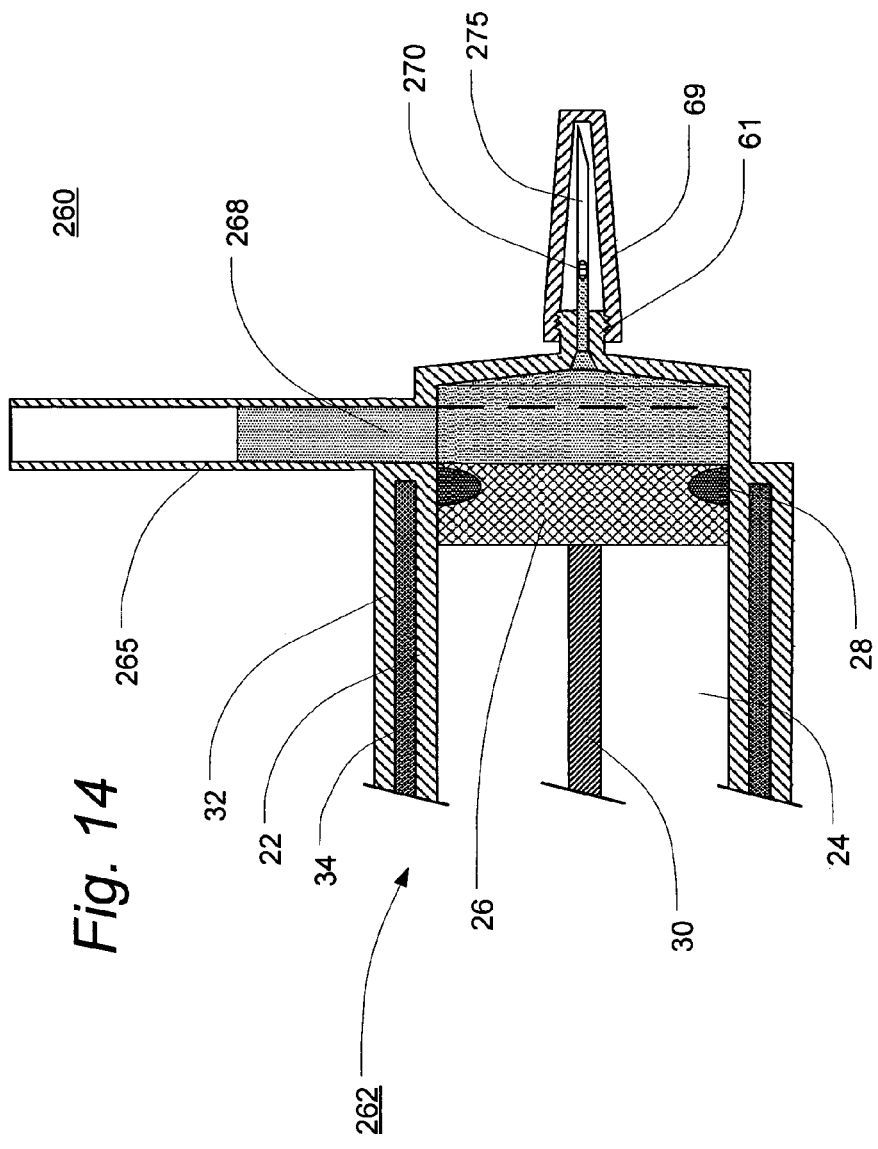
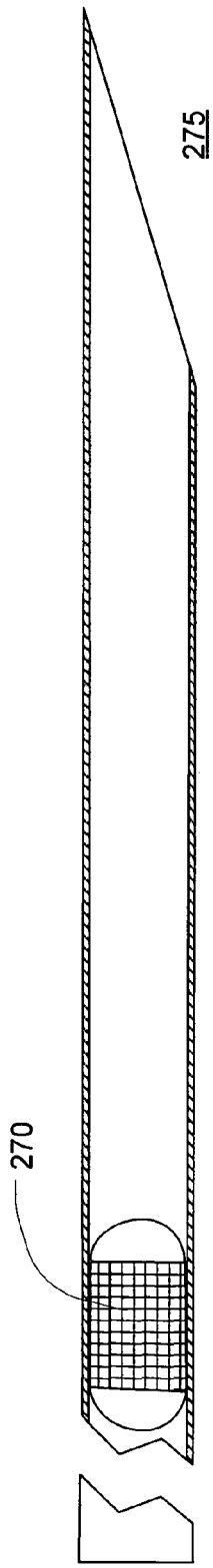
Fig. 14
Fig. 15

UTILIZING LIPOPOLYSACCHARIDE IN EXHALED BREATH CONDENSATE TO DIAGNOSE GRAM NEGATIVE PNEUMONIA

CROSS-REFERENCE TO RELATED APPLICATION

This application claims the benefit of, and claims priority to provisional U.S. Patent Application Ser. No. 60/577,641, filed on Jun. 7, 2004, which is incorporated herein by reference in its entirety.

This application is also a continuation-in-part of U.S. patent application Ser. No. 10/742,721 filed Dec. 19, 2003, which claims the benefit of provisional U.S. Patent Application Ser. No. 60/434,916 filed Dec. 20, 2002 and provisional U.S. Patent Application Ser. No. 60/447,581 filed Feb. 14, 2003. The entirety of each of the aforementioned applications is incorporated herein by reference.

In addition, this is a continuation-in-part of U.S. patent application Ser. No. 10/778,477 filed Feb. 13, 2004, which claims the benefit of provisional U.S. Patent Application Ser. No. 60/447,581 filed Feb. 14, 2003. The entirety of each of the aforementioned applications is likewise incorporated herein by reference.

BACKGROUND OF THE PRESENT INVENTION

1. Field of the Present Invention

The present invention relates generally to a method and devices for diagnosing gram negative bacterial pneumonia and, in particular, to diagnosing gram negative bacterial pneumonia by detecting the presence of lipopolysaccharide in exhaled breath condensate.

2. Background

Pneumonia represents a common disease with significant morbidity and mortality. Pneumonia is the number one cause of death by infectious disease and the sixth most common cause of death in the United States. The National Hospital Ambulatory Medical Care Survey found that in 2001, 1.48 million emergency department visits were related to a diagnosis of pneumonia The National Hospital Discharge Survey found that in 1998, 1.32 million patients were discharged after having been treated for pneumonia.

Pneumonia can be caused by lung infection of many types of microorganisms, including viruses, chlamydia, mycoplasma, protozoa, fungi, and bacteria. For a patient with suspected pneumonia, the clinician has a duty to determine the exact cause of infection because the identity of the infectious agent dictates the choice of antimicrobial treatment. The most common cause in Western society is bacterial pneumonia, and when bacterial pneumonia is suspected, clinicians generally seek to categorize the cause of bacterial pneumonia as Gram positive, Gram negative or anaerobic.

In particular, clinicians are motivated to identify the presence of Gram negative bacterial infection because Gram negative lung infections are aggressive and are associated with higher rates of complications and death. The Gram negative feature of bacteria refers to the color of the bacteria after a staining protocol that will be well understood by those skilled in the art. Gram negative bacterial infections, including gram negative bacterial pneumonia, require specific antimicrobial therapy, which is different from treatment for other types of bacterial infections, and warrant an elevated level of financial reimbursement from third party payors such as Medicare.

In current clinical practice, pneumonia is diagnosed by combining clinical, laboratory and radiographic information. In general, features such as the patient's complaint, the patient's vital signs, the peripheral white blood count, and the results of chest radiography are used to determine the presence or absence of pneumonia. When these sources of data fit a typical pattern, the diagnosis can be made with reasonable clinical certainty, and antimicrobial therapy can be initiated prior to the results of bacteriological cultures. Although nonspecific clinical data is often used to initiate antibiotic treatment for Gram negative infection, common practice dictates that the final diagnosis of Gram negative pneumonia requires more specific evidence of Gram negative bacterial lung infection.

Toward this goal, a Gram's stain can be performed immediately on sputum that is coughed from the lower airways, and microscopic analysis may reveal bacteria with morphology and color suggesting Gram negative infection. However, useful sputum samples are notoriously difficult to obtain from humans with pneumonia. When blood specimen cultures from a patient who has a clinical pattern consistent with pneumonia grow a Gram negative bacterium, this provides a specific indication of Gram negative pneumonia. Unfortunately, more often than not, the blood is sterile in a patient with Gram negative pneumonia.

In addition, a patient's blood may be examined for endotoxin concentration using chemical assays for the endotoxin molecule. However, endotoxin concentrations have been found to be an inaccurate predictor of either the cause or severity of the more general sepsis syndrome. Endotoxin concentrations in the blood may fluctuate widely over short time periods. Further, certain disease states, including liver disease, polytrauma, hypertension, and hematological malignancies are associated with chronically elevated endotoxin concentrations in the absence of clinically significant infection. No study has examined whether circulating endotoxin concentrations can predict a gram negative source of pneumonia.

A sensitive and specific method to diagnose Gram negative lung infection is to perform bronchalveolar lavage and to perform a bacteriological culture on the lavage fluid. Another method is to chemically assay for lipopolysaccharide content in bronchoalveolar lavage samples. Investigators using this method found that high concentrations of lipopolysaccharide are associated with concomitant growth of grain negative bacteria in cultures of the bronchalveolar fluid. A complete description of this method may be found in Flanagan, P. G., Jackson, S. K., Findlay, G., "Diagnosis of Gram negative, ventilator associated pneumonia by assaying endotoxin in bronchial lavage fluid", J. Clin. Pathol. 2001, 54:107-110 and Pugin, J., Auckenthaler, R. and Delaspre, O., "Rapid Diagnosis of gram-negative pneumonia by assay of endotoxin in bronchoalveolar lavage fluid", Thorax 1992, 47:547-549. Both methods have the drawbacks that special endoscopic equipment and subspecialty expertise are required and that they are relatively invasive and uncomfortable procedures. Moreover, known culture methods require at least 24 hours to obtain results. As such, a patient may wait for up to at least 24 hours before receiving an effective antibiotic treatment.

The cell wall of Gram negative bacteria comprises endotoxins. Endotoxins are toxic materials released by bacterium on bacterial lysis. While endotoxins were first recognized for their ability to induce fever, they are now known to have a broad spectrum of biologic activities. On bacteriolysis, endotoxins consisting of aggregates of lipopolysaccharides and protein and lipids, are released from the bacterium into surrounding medium Endotoxins consist primarily of lipopolysaccharide ("LPS") with various amounts of protein and lipid. Since almost all of the biologic activities usually attributable to bacterial endotoxins can also be elicited with isolated chemically pure lipopolysaccharide, the terms "endotoxin" and "lipopolysaccharide" are used interchangeably.

From a pathogenic standpoint, the presence of lipopolysaccharide is one of the most important implications of a Gram negative infection. As such, detecting lipopolysaccharide in a patient's bodily fluid is an indicator of Gram negative bacterial infection. More specifically, the presence of lipopolysaccharide in a patient's bodily fluid is an important potential indicator of Gram negative pneumonia.

The present invention overcomes the above-described clinical disadvantages of diagnosing Gram negative bacterial pneumonia by performing an assay for lipopolysaccharide on the liquid derived from condensation of exhaled breath. Using novel devices and methods described herein, exhaled breath condensate may be obtained from a spontaneously breathing subject via a mouthpiece, facemask or other similar means or from a subject breathing with the assistance of a mechanical ventilator via a connection to the expiratory tubing of the mechanical ventilator. An additional advantage of the present invention is the shorter time period for diagnosing a Gram negative bacterial infection, such as pneumonia, than is required for other diagnostic methods.

Alternative devices for collecting exhaled breath condensate are also known. These devices include those disclosed in Gaston et al., U.S. Pat. Nos. 6,033,368 and 6,419,634; Hunt et al., U.S. Pat. No. 6,585,661; Baddour, U.S. application Ser. No. 10/257,912; and EU Patent No. 0,759,169 B1 to Winsel et al., all of which are incorporated by reference herein in their entireties. In addition, Kline, U.S. application Ser. Nos. 10/742,721 and 10/778,477, two commonly-assigned non-provisional patent applications, disclose devices for collecting exhaled breath and are incorporated by reference herein in their entireties.

Exhaled condensate is known to contain many molecules that can serve as markers of many lung diseases, as reviewed by Kharitinov et al. in 2001 (*Biomarkers* 7 (1): 1-32, 2002.). However, the concept of measuring lipopolysaccharide in exhaled breath condensate for the purpose of diagnosing Gram negative pneumonia or other Gram negative bacterial infections has not been disclosed previously.

SUMMARY OF THE PRESENT INVENTION

The present invention comprises a method for determining whether a subject has Gram negative bacterial pneumonia based on the presence of lipopolysaccharide in exhaled breath condensate collected from the subject. The present invention further comprises the collection devices utilized to collect exhaled breath condensate from both spontaneously breathing and mechanically ventilated subjects and the devices utilized to determine whether lipopolysaccharide is present in the collected exhaled breath condensate.

Broadly defined, the present invention, according to one aspect, is a method for diagnosing and monitoring intrapulmonary Gram negative bacterial infection in an air-breathing vertebrate subject, including: collecting exhaled breath condensate from an air-breathing vertebrate subject; measuring the concentration of lipopolysaccharide in the collected exhaled breath condensate; and determining whether the subject has an intrapulmonary Gram negative bacterial infection based on the measured concentration of lipopolysaccharide in the exhaled breath condensate.

In features of this aspect, the intrapulmonary Gram negative bacterial infection is pneumonia; the intrapulmonary Gram negative bacterial infection is a bronchial infection; the method further includes selecting an antibiotic therapy in response to a positive determination that the subject has an intrapulmonary Gram negative bacterial infection; collecting exhaled breath condensate from an air-breathing vertebrate subject includes collecting exhaled breath condensate from a mammalian subject, and the method further includes monitoring the response of the mammalian subject to antibiotic therapy; the method further includes identifying the particular strain of the intrapulmonary Gram negative bacteria; identifying includes identifying the particular strain of intrapulmonary Gram negative bacteria based upon a determination of the O-saccharide portion of the lipopolysaccharide molecule; measuring the concentration of lipopolysaccharide includes measuring the concentration of lipopolysaccharide using the limulus amoebocyte lysate assay; a measured concentration of lipopolysaccharide of at least about 0.20 Endotoxin Units/mL (EU/mL) indicates the presence of a Gram negative bacterial infection; collecting exhaled breath condensate from an air-breathing vertebrate subject includes collecting the expired breath condensate from a spontaneously breathing subject; collecting exhaled breath condensate from an air-breathing vertebrate subject includes collecting the expired breath condensate from a mechanically ventilated subject; and collecting exhaled breath condensate from an air-breathing vertebrate subject includes utilizing an exhaled breath condensate collection device comprising a chamber having inner walls that may be cooled to a temperature of about 32 degrees Fahrenheit and below to promote condensation.

The present invention, according to another aspect, is a method for diagnosing and monitoring intrapulmonary Gram negative bacterial infection in an air-breathing vertebrate subject, including: collecting exhaled breath condensate from an air-breathing vertebrate subject; providing a reaction chamber, wherein said reaction chamber has a reaction reagent disposed therein; delivering at least a portion of the collected exhaled breath condensate to the reaction chamber; and determining whether the subject has an intrapulmonary Gram negative bacterial infection based on a physical change that occurs when the at least a portion of the collected exhaled breath condensate is delivered to the reaction chamber, wherein said physical change is caused by the presence of lipopolysaccharide in the exhaled breath condensate.

In features of this aspect, the reaction reagent includes a limulus amoebocyte lysate, a chromogenic substrate and/or a fluorogenic substrate; the reaction reagent includes a chemical that liberates heat through an exothermic reaction upon delivery of the at least a portion of the exhaled breath condensate; the physical change is the formation of a gel; the method further includes visually matching a color change in the reaction chamber to a standard, wherein said standard comprises a printed strip of color patches of increasing hue intensity, and wherein each color patch corresponds to increasing concentrations of lipopolysaccharide, respectively; a hue intensity corresponding to a concentration of 0.2 endotoxin units per milliliter indicates the presence of an intrapulmonary Gram negative bacterial infection; collecting exhaled breath condensate from an air-breathing vertebrate subject includes collecting the expired breath condensate from a spontaneously breathing subject; collecting exhaled breath condensate from an air-breathing vertebrate subject includes collecting the expired breath condensate from a mechanically ventilated subject; collecting exhaled breath condensate from an air-breathing vertebrate subject includes utilizing an exhaled breath condensate collection device comprising a chamber having inner walls that may be cooled to a temperature of about 32 degrees Fahrenheit and below to promote condensation; and delivering at least a portion of the exhaled breath condensate comprises injecting at least of portion of the exhaled breath condensate into the reaction chamber via a hypodermic needle.

The present invention, according to another aspect, is a method for diagnosing and monitoring intrapulmonary Gram negative bacterial infection in an air-breathing vertebrate subject, including: collecting exhaled breath condensate from an air-breathing vertebrate subject; providing a reaction chamber with an interior surface, wherein said reaction chamber has a material that binds lipopolysaccharide disposed therein; delivering at least a portion of the collected breath condensate to the reaction chamber; washing the reaction chamber with a buffer; delivering a reaction reagent to the reaction chamber; and determining whether the subject has an intrapulmonary Gram negative bacterial infection based on a physical change that occurs when the at least a portion of the collected exhaled breath condensate is delivered to the reaction chamber, wherein said physical change is caused by the presence of lipopolysaccharide in the exhaled breath condensate.

In features of this aspect, the reaction reagent comprises a chromogenic substrate and/or a fluorogenic substrate; the binding material is an antibody that binds a specific species of lipopolysaccharide; the antibody is disposed on the interior surface of the reaction chamber; the binding material is an insoluble polymer; the binding material is embedded in a matrix surface disposed within the reaction chamber; the method further includes visually matching a color change in the reaction chamber to a standard, wherein said standard comprises a printed strip of color patches of increasing hue intensity, and wherein each color patch corresponds to increasing concentrations of lipopolysaccharide, respectively; a hue-intensity corresponding to a concentration of 0.2 endotoxin units per milliliter indicates the presence of an intrapulmonary Gram negative bacterial infection; collecting exhaled breath condensate from an air-breathing vertebrate subject includes collecting the expired breath condensate from a spontaneously breathing subject; collecting exhaled breath condensate from an air-breathing vertebrate subject includes collecting the expired breath condensate from a mechanically ventilated subject; collecting exhaled breath condensate from an air-breathing vertebrate subject includes utilizing an exhaled breath condensate collection device comprising a chamber having inner walls that may be cooled to a temperature of about 32 degrees Fahrenheit and below to promote condensation; delivering at least a portion of the exhaled breath condensate comprises injecting at least of portion of the exhaled breath condensate into the reaction chamber via a hypodermic needle.

The present invention, according to another aspect, is a method for diagnosing and monitoring intrapulmonary Gram negative bacterial infection in an air-breathing vertebrate subject, including: collecting exhaled breath condensate from an air-breathing vertebrate subject in a collection device having a narrow tube; inserting a fibrous plug impregnated with enzymes that cause gelation upon exposure to lipopolysaccharide into the narrow tube; introducing at least a portion of the collected exhaled breath condensate sample into the narrow tube to wet the fibrous plug; and determining whether the subject has an intrapulmonary Gram negative bacterial infection based on the amount of gelation that occurs in the narrow tube, wherein said gelation is caused by the presence of lipopolysaccharide in the exhaled breath condensate.

In features of this aspect, the fibrous plug is impregnated with enzymes from limulus amoebocyte lysate; the method further includes providing a syringe disposed within the collection device, said syringe having a manometer disposed on one side thereof for measuring hydraulic pressure; and the narrow tube is a hypodermic needle disposed at the end of the syringe.

The present invention, according to another aspect, is a device for collecting exhaled breath condensate from a subject breathing with the assistance of a mechanical ventilation circuit, including: a mechanical ventilation circuit for facilitating breathing of the subject, wherein the mechanical ventilation circuit includes an expiratory flow tube that serves as a conduit for removing exhaled breath of the subject; a central chamber having an interior, wherein said central chamber may be cooled to a temperature of about 32 degrees Fahrenheit and below to promote condensation; a breath input assembly, disposed at one end of the central chamber, in fluid communication with the interior of the central chamber and the expiratory flow tube, whereby the breath input assembly connects the expiratory flow tube and the central chamber; an exit assembly, disposed at the other end of the central chamber, in fluid communication with the interior of the central chamber; and a vacuum device connected to the exit assembly for collecting exhaled breath condensate from the central chamber.

The present invention, according to another aspect, is a breath condensate collection device, including: a central chamber having an interior and first and second opposing ends; a breath input assembly in fluid communication with the interior of the central chamber; and an exit assembly in fluid communication with the interior of the central chamber, wherein the exit assembly includes a narrow tube, said narrow tube having a fibrous plug disposed therein, said plug being impregnated with a reaction reagent that causes gelation upon exposure to lipopolysaccharide.

In features of this aspect, the plug is a fiber matrix impregnated with enzymes from a limulus amoebocyte; and the device further includes a plunger assembly having a piston and a handle, wherein the piston is slidably disposed in the interior of the central chamber and wherein the handle extends from the first end of the central chamber so as to permit the piston to be moved within the central chamber, whereby the collected breath condensate may contact the fibrous plug disposed within the narrow tube.

The present invention, according to another aspect, is a reaction chamber assembly for measuring the concentration of lipopolysaccharide in exhaled breath condensate, including: a reaction chamber; a delivery port for delivery of the exhaled breath condensate into the reaction chamber; a reaction reagent to react with lipopolysaccharide present in the exhaled breath condensate; and a viewing portion to allow for visible detection of a physical change in the reaction chamber.

In features of this aspect, the delivery port is a re-sealable cover that may be punctured with a hypodermic needle for delivery of the exhaled breath condensate; the viewing portion is a transparent wall; the reaction chamber further includes an interior surface, and a lipopolysaccharide-immobilizing agent is bound to at least a portion of the interior surface of the reaction chamber; the lipopolysaccharide-immobilizing agent is selected from the group consisting of monoclonal antibodies, polyclonal antibodies, polymyxin antibiotic, lipopolysaccharide-binding protein and limulus anti-lipopolysaccharide factor; the reaction chamber further includes a chemical disposed within the reaction chamber, wherein the chemical liberates heat upon hydration, whereby a temperature in the range of 34 to 43 degrees Celsius is achieved for a period of 15 to 30 minutes upon hydration of the chemical; the chemical is a salt in a semipermeable matrix; the chemical is a salt in crystalline form; and the chemical is sodium thiosulfate pentahydrate.

The present invention, according to another aspect, is a test kit cartridge for detecting the presence of lipopolysaccharide in exhaled breath condensate, including: a housing; a test module disposed within the housing, said test module utilizing a user-initiated chemical reaction to detect the presence of lipopolysaccharide in the exhaled breath condensate; and a positive control module disposed within the housing adjacent to the test module, said positive control module having lipopolysaccharide disposed therein for showing a definite positive result for the presence of lipopolysaccharide for comparison with the test module.

In features of this aspect, a chemical disposed in the housing provides a controlled exothermic reaction, whereby a temperature between 34 and 43 degrees Celsius is achieved for a period of 15 to 30 minutes; the chemical is sodium thiosulfate pentahydrate; each module of the test kit includes a re-sealable injection port, a reaction well, a fluid connection between the reaction well and the injection port, a first one-way valve disposed in the fluid connection, an exit tube providing an outlet for the reaction well, and a second one-way valve disposed in the exit tube; each reaction well includes a clear covering adapted to allow visual determination of physical change; each reaction well includes an insoluble polymeric lipopolysaccharide-binding matrix; the positive control module reaction well includes lipopolysaccharide from a suitable species of Gram negative bacteria; the test kit cartridge further includes a chromogenic substrate, reconstituted from a reaction chamber; the test kit cartridge further includes a color strip, the color strip having color patches of incrementally increasing color intensity, wherein each color patch corresponds to a prescribed range of endotoxin units to allow for visual comparison against a color change in the reaction wells; the housing is formed from a polymer; the polymer is plastic.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein:

FIGS. 10A-10D are partial side cross-sectional views of the first alternative reaction chamber device of FIG. 9;

FIG. 12 is a side cross-sectional view of the test module of FIG. 11, taken along line 12-12;

FIG. 13 is a side cross-sectional view of the positive control module of FIG. 11, taken along line 13-13;

FIG. 14 is a partial side cross-sectional view of a breath condensate collection device in accordance with a fourth preferred embodiment of the present invention;

FIG. 15 is an enlarged partial side cross-sectional view of the needle of FIG. 14.

DETAILED DESCRIPTION OF THE PREFERRED EMBODIMENTS

Figure 1:
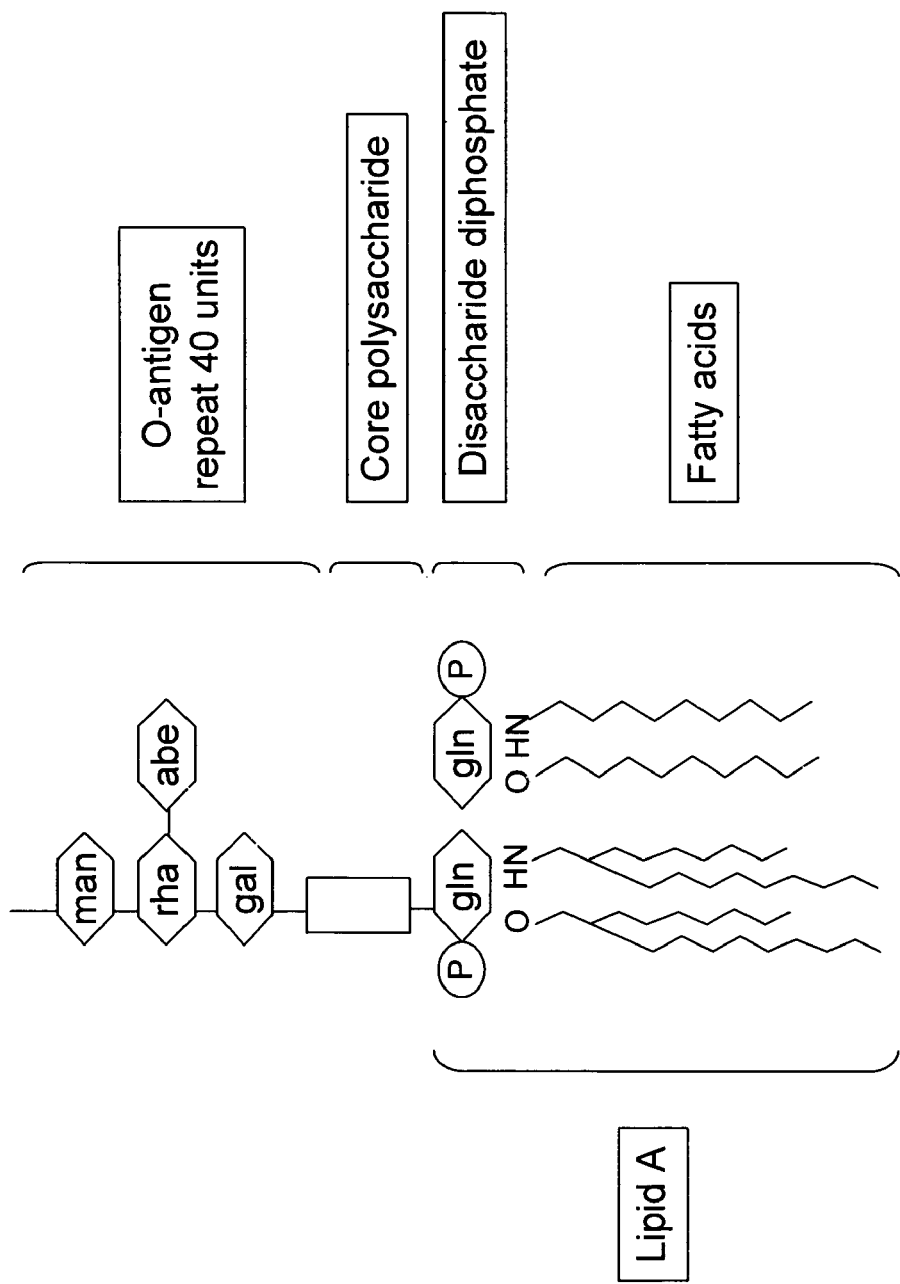
FIG. 1 is a schematic diagram of the basic structure of lipopolysaccharide.

The method of the present invention utilizes exhaled breath condensate to determine whether LPS is present in the exhaled breath condensate and thus determine whether a subject has an intrapulmonary Gram negative bacterial infection. The present application is directed toward diagnosing Gram negative bacterial pneumonia; however, one of ordinary skill in the art will understand that the present invention may be utilized to detect any Gram negative bacterial infection, which is also useful. A patient diagnosed with a Gram negative bacterial infection will be treated with the same antimicrobial therapy whether the diagnosis is Gram negative pneumonia or another Gram negative bacterial infection. One of ordinary skill in the art will understand that while the methodology for detecting LPS, as described herein, is the limulus amoebocyte lysate assay, any methodology for detecting the presence of LPS, including, but not limited to the ELISA assay and the rabbit pyrogen test, may be utilized in the present invention.

Intrapulmonary LPS content can vary based upon the health of the lung in the subject providing a breath condensate sample. Generally, a concentration of LPS in exhaled breath condensate of at least about 0.2 EU/mL corresponds to a clinical test positive threshold, indicating the presence of Gram negative bacterial infection in the lungs. An EU is an endotoxin unit. The USDA recommends reporting the concentration of endotoxin in endotoxin units because an EU can be standardized, unlike typical mass concentrations, which cannot be standardized because of the variable potency of lipopolysaccharide, which varies between bacteria type. An endotoxin unit refers to the amount of LPS reactivity contained in the unknown sample. This amount of reactivity is determined by interpolation from a standard curve, which is derived from an FDA-approved strain of *E-Coli* that has a known amount of LPS reactivity.

It is possible for the device used to collect exhaled breath condensate to contain a "background" level of LPS due to naturally occurring LPS. In order to account for this background concentration, a "mock" standard may be conducted with the device that will be used for exhaled breath collection by instilling LPS-free water through the device. The LPS concentration values found in the water sample may then be subtracted from the LPS concentration values found in breath condensate samples to remove the background "noise" of the system. The background concentration of LPS will vary depending on the device being used for collection.

A breath condensate collection device, several examples of which are described herein below in further detail, may be used to collect exhaled breath condensate from a patient presenting symptoms synonymous with Gram negative bacterial pneumonia for detection of LPS content in amounts indicating infection.

Referring now to the drawings, in which like numerals represent like components throughout the several views, the preferred embodiments of the present invention are next described. The following description of the preferred embodiment(s) is merely exemplary in nature and is in no way intended to limit the invention, its application, or uses.

FIG. 1 is a schematic diagram of the basic structure of lipopolysaccharide. This structure is found in the cell wall of all Gram negative bacteria. Lipopolysaccharide (also referred to as endotoxin) is a complex glycolipid, weighing approximately 10 Kd. The basic structure of lipopolysaccharide involves three relatively well defined regions and is similar in all gram-negative bacteria. These regions are an O-antigen portion, a core polysaccharide and lipid A. The O-antigen portion is composed of repeating polysaccharide units, each having 2-6 saccharides. The O-antigen portion varies considerably among Gram negative species and can thus serve as a marker of individual bacterial species, based upon binding of specific monoclonal antibodies. The core lies between the O-antigen portion and lipid A and is a branching polysaccharide having representative sugars such as glucose, N-acetylglucosamine and galactose. Unlike the O-antigen portion, there is only minor variation throughout the core region with the structure being highly conserved in the inner core region proximal to lipid A. The most highly conserved portion of the LPS molecule is lipid A, a disaccharide diphosphate, to which long-chain fatty acids are attached. The lipid A portion of the molecule confers toxicity in virtually all complex eukariotic organisms. In humans, this includes induction of cytokines, fever, leukocytosis, recruitment and activation of leukocytes, vascular damage, vasodilation, intravascular coagulation and organ damage.

One accepted method of detecting and quantifying LPS takes advantage of the toxic effect of LPS on the aqueous extract of amoebocytes from the horsehoe crab, *limulus polyphemus*. The term "amoebocytes," as used in the present application, refers to blood cells. This method, known generally as the limulus amoebocyte lysate ("LAL") assay, is described in U.S. Pat. Nos. 4,322,217; 5,310,657 and 5,702,882. Other recognized methods include the in-vivo rabbit pyrogen assay and the human pyrogen assay, which are well known to those skilled in the art and thus, will not be discussed in detail herein.

Briefly summarized, LAL forms a coagulen gel when incubated with LPS, which enables the detection of small quantities of LPS. More specifically, in the LAL assay, LPS activates an enzyme, commonly known as factor C, which is contained in the amoebocytes. Activated factor C, in turn, activates factor B by hydrolyzing a specific site of factor B. Activated factor B activates a proclotting enzyme to convert it into a clotting enzyme. The clotting enzyme then cleaves coagulogen (coagulant protein, molecular weight: 19,723) at specific sites (i.e., $Arg^8$-$Thr^{19}$ and $Arg^{46}$-$Gly^{47}$) to cause gelation of the mixture. In addition, co-factors such as salts of calcium, magnesium and phosphate or other organic compounds such as hydroxymethyl ("TRIS") aminomethane buffer must be present to maintain a pH between 6.5 and 7.4, enabling the clotting enzyme to function.

Various techniques have been utilized to detect LPS based on the formation of a coagulen gel in the LAL assay. Some are endpoint assays that simply wait for the formation of a gel to determine the presence of LPS. Others are more complex and use kinetic turbidimetric methods to measure the increase in turbidity as coagulation occurs in the LAL assay.

An alternative assay methodology using chromogenic or fluorogenic substrates has also been used to detect LPS in order to overcome difficulties associated with accurately determining gel formation. This alternative methodology relies on the clotting enzyme that was formed in the above cascade reaction hydrolyzing an amide bond in a synthetic substrate. The synthetic substrate may be covalently attached to a marker molecule or compound, which is liberated when hydrolyzed by the clotting enzyme. The liberated marker may then be detected by colorimetry or spectrophotometry, thus indicating the presence of LPS. Examples of synthetic substrates may include, but are not limited, t-butoxycarbonyl-leucyl-glycyl-arginine-paranitroanilide (N-t-Boc-Leu-Gly-Arg-pNA), N-t-Boc-Val-Leu-Gly-Arg-pNA (SEQ ID NO: 1), benzyloxycarbonyl-leucyl-glycyl-arginine-paranitroanilide (Z-Leu-Gly-Arg-pNA), Boc-Ile-Glu-Gly-Arg-pNA (SEQ ID NO: 2), Boc-Val-Ser-Gly-Arg-pNA (SEQ ID NO: 3) or Boc-Ser-Gly-Arg-pNA, all of which liberate paranitroaniline, which imparts a yellow color to the reaction mixture. Specific examples of chromogenic assays are described in Ling, U.S. Pat. No. 6,645,724, and Tamura et al., U.S. Pat. No. 5,702,882.

It is also possible to synthesize the enzyme needed for the clotting cascade in-vitro by recombinant biotechnology rather than obtaining the enzyme from a horseshoe crab. Such synthesized enzyme can be used to detect and quantify LPS in an unknown solution using the chromogenic method.

Other alternate methods of capturing and detecting LPS are also known. An LPS binding material, e.g., polymyxin antibiotics or resins, in the form of an insoluble matrix polymer, may be affixed to a support for immobilization and subsequent detection of LPS by any of the above described turbidimetric, chromogenic or fluorogenic methods. In addition, LPS may be immobilized by any number of antibodies with a high affinity for LPS. Antibodies have a Y-shaped structure and include two basic units. The first unit is the fragment-antigen binding portion ("Fab") and it binds an antigen, in this situation, LPS. The second unit is the fragment-crystallized portion ("Fc"). The Fc unit can function as a handle to dock the antibody to an immobile surface. Potentially useful antibodies include, but are not limited to, polyclonal or monoclonal antibodies, such as lipid-A reactive monoclonal antibody ("HA-1A") and murine anti-endotoxin immunoglobulin M ("E5"), lipopolysaccharide-binding protein ("LBP") and related proteins, bacteriocidal/permeability increasing protein ("BPI") and limulus anti-LPS factor ("LALF").

A method utilizing enzyme-linked immunoassay technology is also known in which various selected matrix-bound antibodies may be used to capture and detect specific endotoxins and therefore specific bacteria types. Examples of endotoxin from bacteria that may be detected, include, but are not limited to, *Escherichia, Bordetilla, Branhamella, Salmonella, Haemophilus, Klebsiella, Proteus, Enterobacter, Pseudomonas, Pasteurella, Acinetrobacter, Chlamydia* and *Neisseria* and in general any bacteria whose LPS is capable of binding to the selected antibody.

It is further recognized that the presence of β-1,3 glucans (β-D-glucans) may also activate the above-described clotting cascade. One of ordinary skill in the art will understand that specific measures may be undertaken to limit this false positive effect.

The present invention includes several collection devices designed to allow rapid (e.g., less than 30 minutes), noninvasive collection of exhaled breath condensate ("EBC") from a spontaneously breathing subject or a patient receiving mechanical ventilation, followed by one-step quantitative or semi-quantitative analysis of the condensate for the concentration of LPS. In spontaneously breathing subjects, the exhaled condensate may generally be collected via a mouthpiece held by the lips; however, in patients with severe respiratory distress, the sample may be collected by fitting the patient with an airtight, snug-fitting facemask that allows the delivery of oxygen, while allowing the diversion of exhaled gases and aerosol into a condensing chamber such as those described below.

In general, the breath condensate collection devices each comprise a collection chamber that has sterile, LPS-free inner walls that can be cooled to a temperature below 32° F. to allow condensation of exhaled breath. These breath condensate collection devices are preferably disposable and lightweight. Each includes coaxial chambers with an interposed area containing coolant that can be chilled externally or via an internal endothermic reaction. Such breath condensate collection devices are generally described in the aforementioned commonly-developed and commonly-assigned U.S. patent application Ser. Nos. 10/42,721 and 10/778,477. However, the devices described and illustrated herein have additional novel and useful features not included in any prior art devices.

Figure 2:
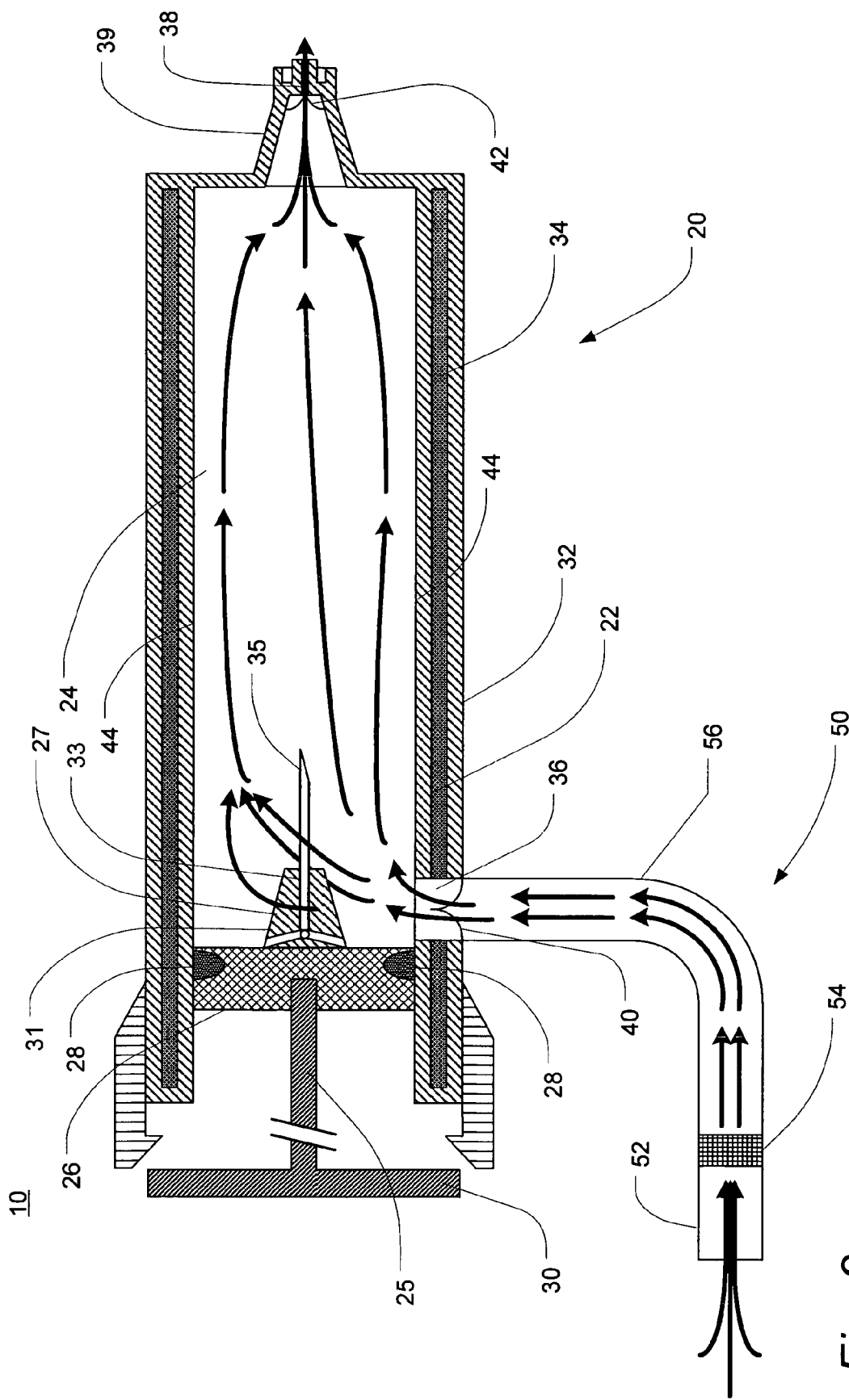
FIG. 2 is a side cross-sectional schematic view of a breath condensate collection device in accordance with a first preferred embodiment of the present invention.

FIG. 2 is a side cross-sectional schematic view of a breath condensate collection device 10 in accordance with a preferred embodiment of the present invention. This configuration may be particularly appropriate for use with cooperative humans. The breath condensate collection device 10 includes a double-walled syringe 20 and a breath input assembly 50. The inner wall 22 of the syringe 20 defines a cylindrical central chamber 24 in which is fitted a plunger assembly 25 that includes a piston 26, a rubber gasket 28 and a handle 30 extending from one end of the syringe 20. The outer wall 32 is arranged around the inner wall 22 in such a way as to create a narrow space between the inner and outer walls 22, 32. During manufacture, the space between the inner and outer walls 22, 32 may be filled with a jacket of coolant material 34, and the outer wall 32 may then be sealed to the inner wall 22 to prevent leakage. In a preferred embodiment, water may be used as the coolant material 34, but it should be clear that other materials may likewise be used, such as polyethylene glycol ("PEG") and the like.

The syringe 20 further includes an inlet 36, an outlet 38 and a pair of one-way valves 40, 42. The first valve 40 is an intake valve that may be disposed in or adjacent to the inlet 36, while the second valve 42 is an exit valve that may be disposed in or adjacent to the outlet 38 in order to facilitate the passage of exhaled air through the central chamber 24 in only a single direction. The outlet 38 is preferably disposed at the end opposite the plunger handle 30 in order to permit materials collected within the central chamber 24 to be expressed through the outlet 38 by the piston 26. The outlet 38 may be disposed in the end of a nozzle 39 that is in the form of a nipple. The nozzle 39 may also include a fitting, such as the female portion of a luer lock, at its distal end. Such a fitting may permit a protective cover or other accessory to be attached to the nozzle 39. The valves 40, 42 are illustrated only schematically in the various drawings, but they may, for example, include two or three self-sealing leaves formed from plastic or another deformable polymer. The design of such valves would be apparent to those of ordinary skill in the art.

The piston 26 includes a tip or protrusion 27 of dimensions and shape suitable for fitting snugly into the nozzle 39 when the plunger assembly 25 is fully depressed. The tip 27 includes a plurality of radial conduits 31 arranged around the base of the tip 27 and connecting to a hollow central shaft or conduit 33 in which is disposed a needle 35, such as a hypodermic needle. The radial conduits 31 and the central conduit 33 are preferably between about 1 and 2 mm in diameter, and the outside diameter of the needle 35 is likewise preferably between about 1 and 2 mm in diameter in order to fit snugly into the central conduit 33.

Further, because the piston 26 fills one end of the syringe 20 and the outlet 38 is disposed in the opposite end, the inlet 36 is preferably arranged to penetrate both the inner and outer walls 22, 32 on the side of the syringe 20. In order to cause the most interaction between exhaled air passing through the central chamber 24 and the inner surfaces 44 of the inner wall 22, the inlet 36 is preferably disposed as close to the piston 26 as possible; however, it will be clear that other arrangements of these components are likewise possible without departing from the scope of the present invention.

The breath input assembly 50 includes a mouthpiece 52, a filter 54 and any tubing 56 necessary to guide exhaled breath from the mouthpiece 52 to the inlet 36 of the syringe 20. The mouthpiece 52 is of suitable size and shape so as to permit comfortable contact with the mouth area of a patient. The filter 54, which may comprise a polymer material having perforations or successive intrusions therein, may be arranged within the tubing 56 between the mouthpiece 52 and the syringe inlet 36 to prevent saliva and other liquid or solid matter of a minimum size from passing therethrough and into the syringe 20. Saliva may be further prevented from reaching the central chamber 24 by arranging the breath input assembly 50 beneath the syringe 20, so that air passing through the breath input assembly 50 moves upward. In this arrangement, the effect of gravity on the saliva and other liquid or solid matter helps to prevent such matter from passing up into the central chamber 24, as it instead tends to collect in the tubing 56.

The tubing 56 is preferably configured so as to avoid interference between the mouthpiece 52, or any other part of the tubing 56, and the operation of the plunger assembly 25, as such operation is described herein. More preferably, the mouthpiece 52 is oriented to be generally parallel with the syringe 20 and the plunger assembly 25 therein, or in other words, the mouthpiece 52 is oriented in parallel to the main axis defined by the syringe 20. In this orientation, exhaled breath may be received from a patient without causing interference to the operation of the plunger assembly 25, and condensate formed on the inside of the syringe 20 as the patient uses the device 10 will tend to drain downward toward the outlet 38.

The dimensions of the device 10 are chosen so that a sufficient volume of condensate may be collected in a relatively short period of time using a device 10 that is small and light enough to be easily held by a patient or attendant and that does not require the patient to change his breathing patterns. The walls 22, 32 and other structures of the device 10 are preferably constructed of a material that tends not to bind to proteins, such as platinum-cured silicon. Other suitable materials may include, but are not limited to, glass, plastic, polyethylene, polycarbonate, or polyvinyl or other synthetic polymer. The plunger assembly 25 is likewise preferably constructed from a non-protein-binding material, but may be constructed from any suitable inert material including, but not limited to, plastic, vinyl, polyethylene, rubber, platinum-cured silicon or a fluorine-containing polymer. In addition, TEFLON®, which is a fluorine-containing polymer and is a registered trademark owned by E.I. Du Pont De Nemours and Company Corporation of Wilmington, Del., may be used. In a preferred embodiment, the syringe 20 is between 10 and 20 cm long with a diameter of between 2 and 5 cm. The thickness of the coolant jacket 34 may be between 1 and 10 mm, and the sample volume, expressed from a single use, is preferably between 100 µL and 1000 µL, although it may be possible to obtain useful results from samples as small as 25 µL.

The plunger assembly 25 is modified relative to the plunger assemblies disclosed in prior applications through the inclusion of the hypodermic needle 35, described previously, or a similar structure. This modification facilitates the sterile delivery of condensate into a specialized reaction chamber device, examples of which are described below. The needle 35 is centrally disposed in the central conduit 33 of the piston tip 27, and the interior of the needle 35 is arranged in fluid communication with the radial conduits 31 in the tip 27 for a purpose made evident hereinbelow.

In operation, one or more syringes 20 are first stored in a refrigeration device, such as a conventional household or commercial freezer, that is capable of lowering the temperature to approximately 0° F., thus freezing the jacket of coolant material 34 contained between the inner and outer walls 22, 32 of the syringe 20. When a patient is to be examined, a single syringe 20 is first withdrawn from the freezer. If the breath input assembly 50 or mouthpiece 52 is stored separately from the rest of the device 10, then the device 10 is assembled for use by coupling the various components together. Next, the patient positions the mouthpiece 52 in a sealed relationship to his mouth area and exhales into the mouthpiece 52. The exhaled breath is guided through the tubing 56 and into the central chamber 24 via the inlet 36. The intake valve 40 is forced open by positive pressure, but in the absence of such pressure, it prevents air within the central chamber 24 from escaping through the inlet 36. The exhaled breath then exits through the outlet 38, on the end of the chamber 24 opposite the intake end via the needle 35. The exit valve 42 permits air to pass out of the central chamber 24 only when positive pressure exists on the cylinder side of the valve 42, while in the absence of such pressure, the valve 42 prevents ambient air from entering the central chamber 24 via the outlet 38.

As the patient exhales through the device 10, the moisture in the exhaled breath begins to condense on the inner surfaces 44 of the central chamber 24. Because of the depressed temperature of the coolant 34 and the syringe 20, the condensate may freeze immediately on the inner surface 44. The diameters of the nozzle 39 and the needle 35 are small enough to cause resistance to the exhalation of the patient. The diameters may be preferably chosen so as to slow the rate of expiration until each exhalation requires approximately 5 seconds to complete or until a resistance of up to about 5 cm of water pressure is provided. It will be apparent to one of ordinary skill in the art that the nozzle 39 may alternatively be fitted with a positive end-expiratory pressure valve (a "PEEP" valve), which has a dial to vary the resistance to exhalation. PEEP valves are commercially available from Life Assist Inc, Rancho Cordova, Calif. This modification would increase the amount of time for exhaled breath to equilibrate with the inside surfaces 44 of the central chamber 24.

As the patient continues to exhale through the device 10, the frozen coolant 34 disposed in the space between the inner wall 22 and outer wall 32 of the device 10 begins to melt. The composition, volume and thickness of the coolant jacket 34 surrounding the central chamber 24 is preferably calibrated such that the coolant 34 begins to melt after approximately 10-15 exhalations by the patient. Once the coolant 34 melts or thaws after the desired number of exhalations, the condensate likewise can begin to melt. Once the condensate is melted, the plunger assembly 25 may be depressed to express the collected condensate sample through the outlet 38.

Figures 3A, 3B:
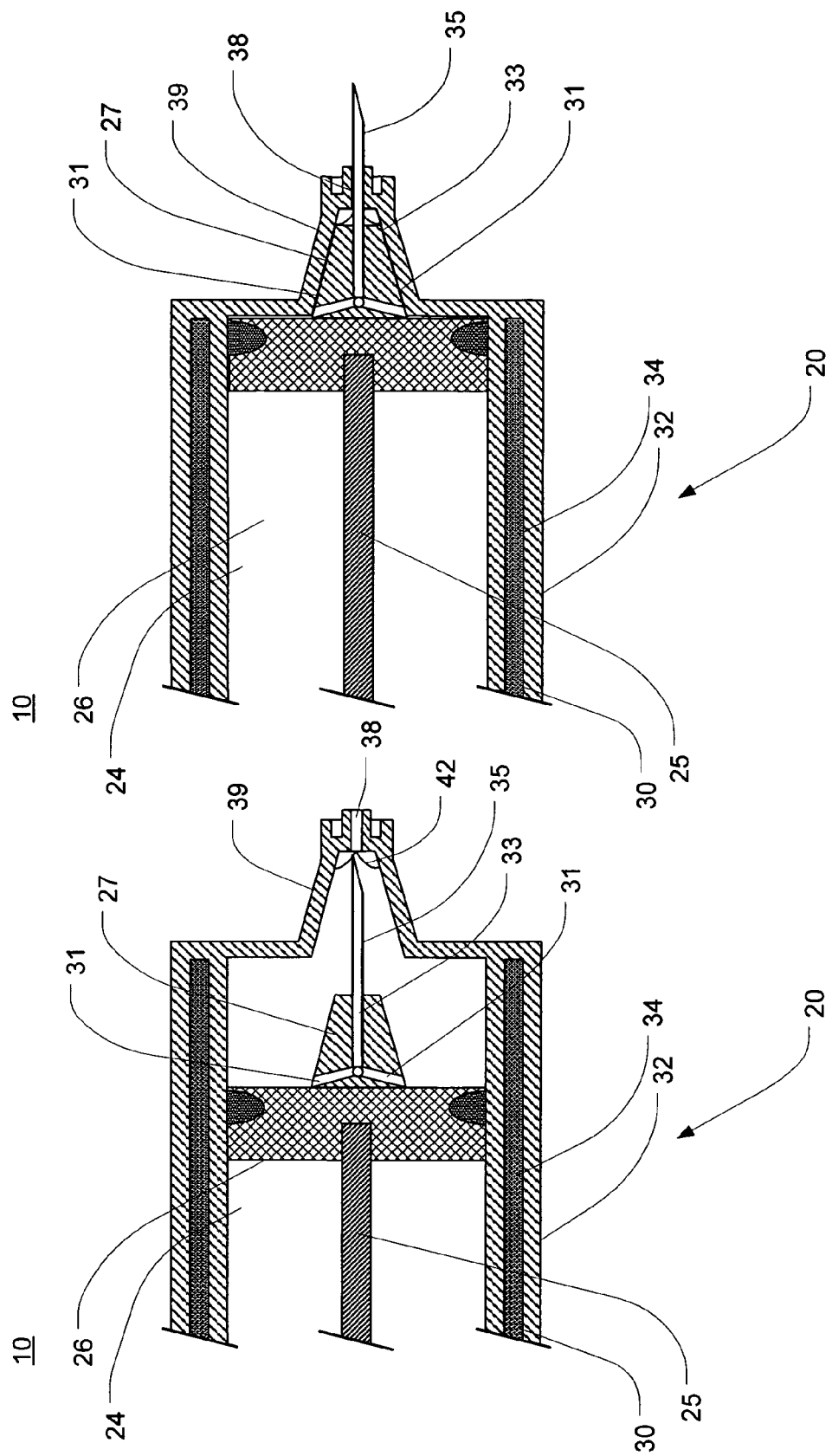
FIG. 3A is a partial side cross-sectional schematic view of the breath condensate collection device of FIG. 2 with the plunger assembly in a partially depressed position.
FIG. 3B is a partial side cross-sectional schematic view of the breath condensate collection device of FIG. 2 with the plunger assembly in a fully depressed position.

FIGS. 3A and 3B are partial side cross-sectional schematic views of the breath condensate collection device 10 of FIG. 2 with the plunger assembly 25 in a partially depressed position and a fully depressed position, respectively. As the plunger assembly 25 is depressed, the needle 35 is forced through the outlet 38. Meanwhile, as the volume of the space between the piston 26 and the outlet 38 shrinks, condensate is forced through the radial conduits 31 to the central conduit 33 and from there into the hypodermic needle 35. The condensate is then ready for ejection into a suitable reaction chamber device, several examples of which are described below with reference to FIGS. 7-13. Ejection may be facilitated by complete depression of the plunger assembly 25. A clip assembly may be provided at the opposite end of the syringe 20 in order to capture the handle 30 of the plunger assembly 25, thereby providing an indication to the user that the plunger assembly 25 has been fully depressed. Finally, once the EBC has been collected and ejected via the needle 35 in accordance with the test procedures described hereinbelow, the entire device 10 may be disposed of according to conventional waste disposition procedures.

Figure 4:
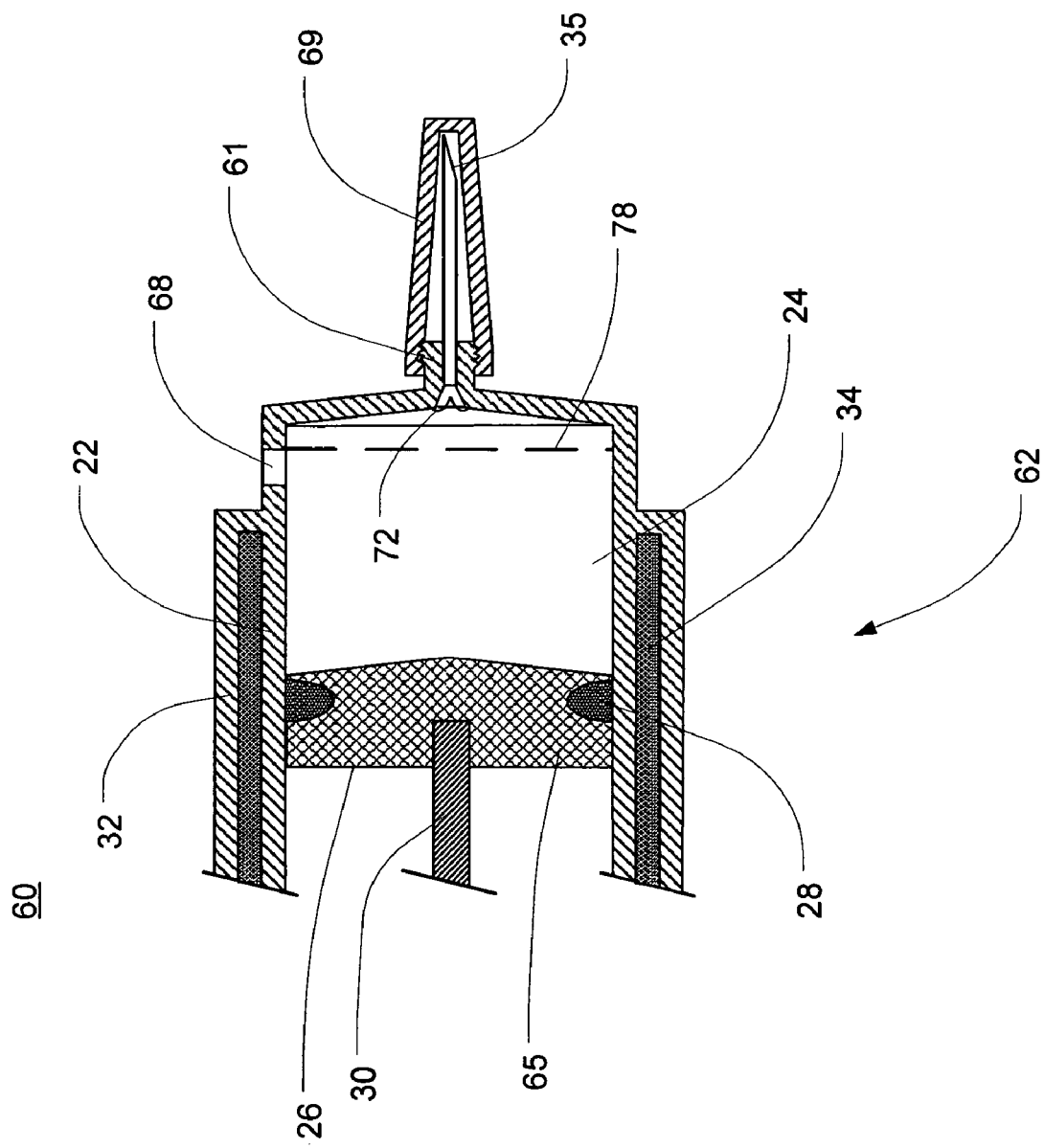
FIG. 4 is a partial side cross-sectional view of a breath condensate collection device in accordance with a second preferred embodiment of the present invention.

FIG. 4 is a partial side cross-sectional view of a breath condensate collection device 60 in accordance with a second preferred embodiment of the present invention. Like the first embodiment, this breath condensate collection device 60 includes a double-walled syringe 62, which includes a central chamber 24, a plunger assembly 65, a rubber gasket 28 and a handle 30, and a breath input assembly (not shown). The body of the syringe 62, including the central chamber 24 and the various components thereof, are similar to those of the first syringe 20 with several significant exceptions. First, the outlet 38 of the first embodiment is replaced with an bleed port 68, approximately 1 mm in diameter, penetrating the inner and outer walls 22, 32 of the syringe 62 near the distal end thereof. The bleed port 68 allows air to escape from the central chamber 24 as the plunger assembly is depressed but retains the EBC. Also, the plunger assembly 65 does not include a nipple-shaped tip on the face of the piston 66 or a needle extending therefrom. However, the face of the piston 66 does have a slight conical shape, and the end of the central chamber 24 is correspondingly-shaped. Together, this configuration may guide collected condensate to the outlet 38 more efficiently. It will be apparent, however, that the nipple-shaped tip 27 of the previous device 10 and the conical shape disclosed in the device of FIG. 4 are not mutually exclusive, and that the conical shape may easily be incorporated into the device of FIG. 2, i.e, by combining the nipple-shaped tip 27 of FIG. 2 with the conical shape of FIG. 4.

Another difference between the first and second devices 10, 60 is that the second device includes a threaded nozzle 61 in which may be fixed a hypodermic needle 35. The needle 35 is similar to the needle 35 of the first device 10, but is fixed in the nozzle 61 rather than being mounted on the plunger assembly 65. The interior of the needle 35 is communicatively connected to the interior of the central chamber 24. The needle 35 may be protected by a removable plastic covering 69 having a threaded fitting that facilitates easy connection and removal of the covering 69 from the threaded nozzle 61.

When attached to the syringe 62, the covering 69 preferably provides a relatively air-tight seal for a purpose described below.

Use of this second device 60 is somewhat similar to that of the first device 10, although the covering 69 must be removed before the subject may breathe through the needle 35. However, the modifications described above may make this device 60 better Adapted to deliver a calibrated amount of condensate than the first device 10. Once the subject has taken a sufficient number of breaths through the device 60 to ensure that a minimum volume of condensate has been collected, the covering 69 may be replaced on the end of the syringe 62, and the plunger assembly 65 may be carefully depressed. Although the covering 69 effectively prevents gas or liquid from passing through the needle 35, the bleed port 68, which is of conventional design, permits egress of air and any excess condensate until the face of the piston 66 passes the calibration line 78. If desired, a cotton ball or other absorbent material, and an appropriate support structure if desired, may be disposed over the bleed port 68 in order to prevent EBC from escaping to the environment. By holding the device 60 with the bleed port 68 oriented in an upward direction, most or all air may be removed from the central chamber 24, and a calibrated volume of condensate is left therein as measured by the calibration line 78. As shown in FIG. 4, the syringe 62 may use a single wall design in the region of the calibration line 78 in order to make it easier to see the liquid contained therein. Preferably, the syringe 62 is calibrated to collect a volume of between 250 and 500 µL. The covering 69 may then be removed again and this calibrated volume may be delivered by the needle 35 into a suitable reaction chamber device.

Figure 5:
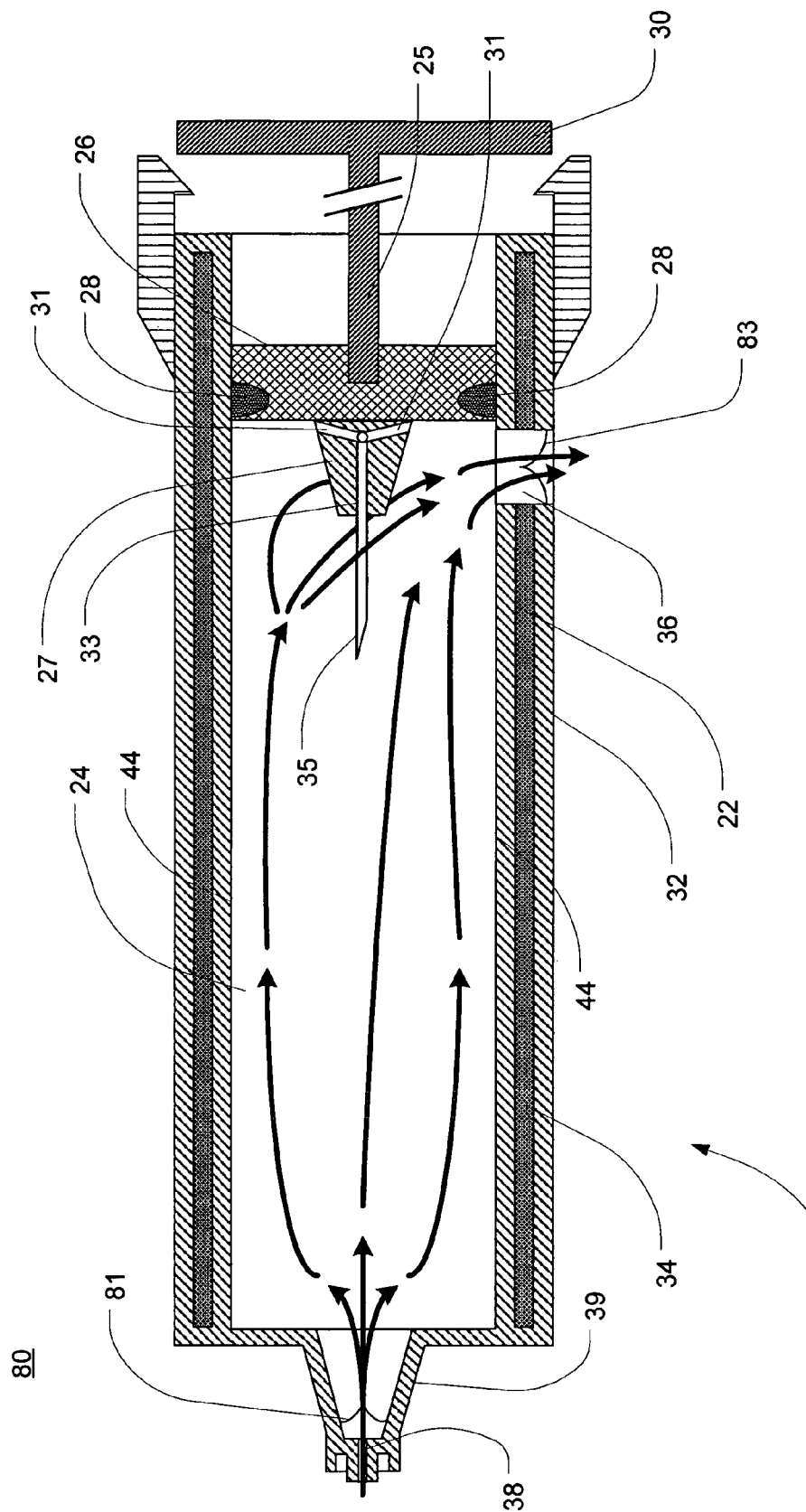
FIG. 5 is a side cross-sectional schematic view of a breath condensate collection device in accordance with a third preferred embodiment of the present invention.

FIG. 5 is a side cross-sectional schematic view of a breath condensate collection device 80 in accordance with a third preferred embodiment of the present invention. It may be advantageous to fractionate exhaled breath into airway and alveolar components, to allow condensation to occur only from the portion of breath originating from the alveoli. This partitioning step may help distinguish lower tract lung infection from bronchitis. As described in the aforementioned U.S. patent application Ser. No. 10/778,477 to Kline, a device for collection of exhaled alveolar breath condensate may incorporate a gating mechanism actuated, for example, by a rise in the partial pressure of exhaled carbon dioxide. The breath condensate collection device 80 illustrated in FIG. 5 is an example of a device suitable for use in the preferred embodiments of that device or in comparable devices. The device 80 of FIG. 5 is similar to the device 10 of FIG. 2 except that the breath input assembly 50 of the first device 10 has been removed to permit the device 80 to be inserted into a housing such as that included in the device disclosed in U.S. patent application Ser. No. 10/778,477. The direction of airflow during the condensation process may also be reversed, as shown in FIG. 5, either to facilitate fluid communication from the gating mechanism or for other purposes, as will be apparent to those of ordinary skill in the art. In this case, the respective positions of the outlet 36 and inlet 38, and their respective one-way valves 81, 83, are now reversed with respect to the device 10 of FIG. 2.

Although not illustrated herein, airflow reversal may also be applied to the device 60 shown in FIG. 4. Even with the airflow direction reversed, however, the condensate may still be delivered into a reaction chamber device via the hypodermic needle 35 as described with regard to either FIGS. 3A and 3B or FIG. 4.

In the preceding embodiments, the respective devices 10, 60, 80 are designed for the collection of EBC from spontaneously breathing subjects, where the subject exhales via a mouthpiece or facemask (not shown) into tubing that directs flow into the appropriate entry port, such as the ones diagrammed in FIG. 2 or FIG. 5. It would also be advantageous for the present invention to be adapted to allow collection from patients being ventilated mechanically. In most hospitals, humans are ventilated against pressurized air, often enriched with oxygen and humidified with excess water vapor. This excess water vapor causes condensation to accumulate in the outflow tubing that directs the exhaled breath away from the patient's lungs during the respiratory cycle. It is a standard practice for respiratory therapists to affix a small cylinder, of approximately 20-100 mL volume, to collect this condensate in the most dependent portion of the exhalation circuit. To take advantage of the present invention to diagnose Gram negative bacterial lung infection in a ventilated patient, an aliquot of the collected condensate may be analyzed for LPS content. In the simplest embodiment, a commercially available syringe of a type used for drug delivery (e.g., an insulin syringe) may be used to withdraw a set volume of condensate (e.g., 100-200 microliters) found in the condensate reservoir in the exhalation line of the ventilation circuit, and this volume could be injected into a reaction chamber device, examples of which are described hereinbelow.

Figure 6:
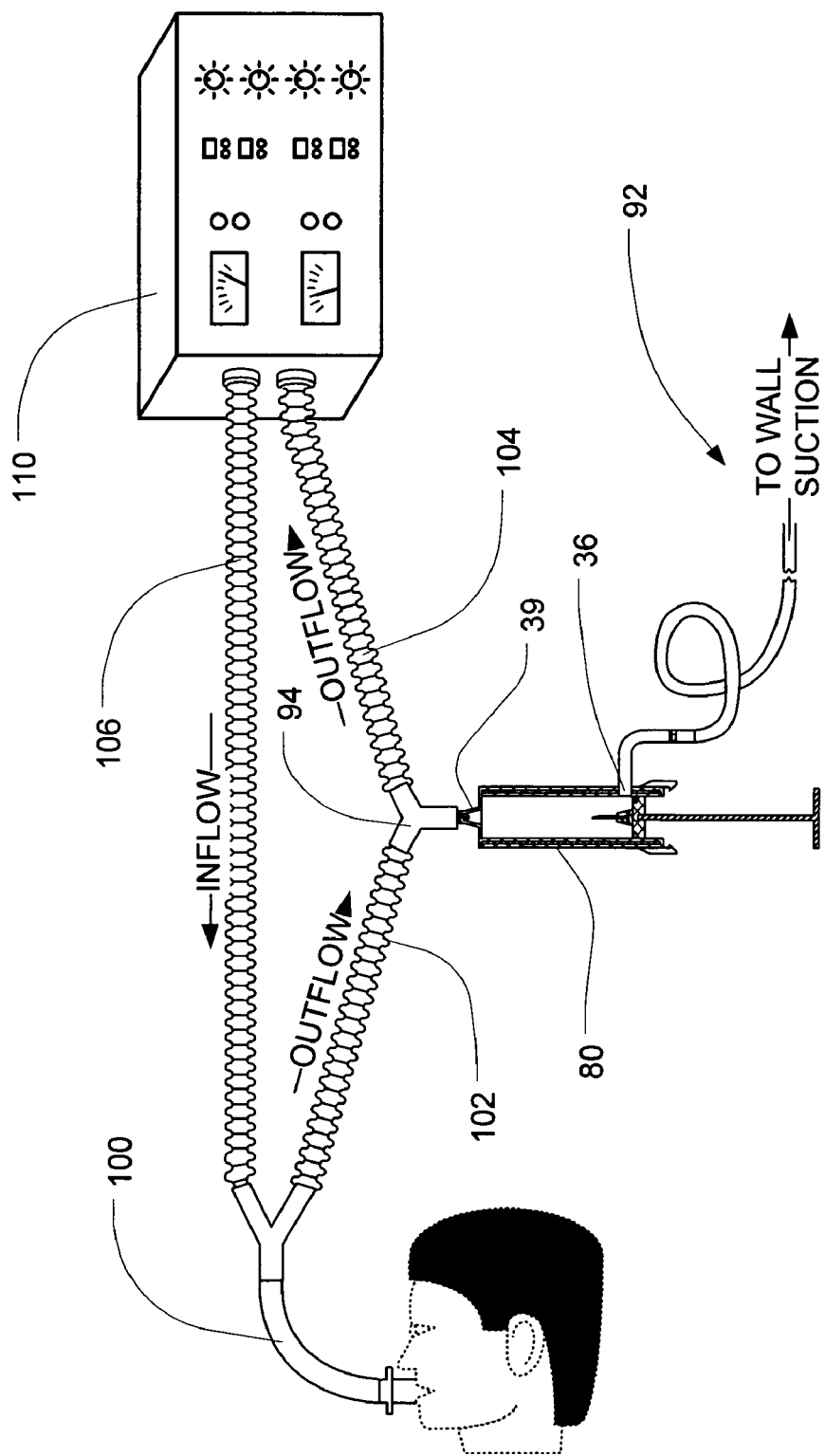
FIG. 6 is a schematic illustration of an alternative ventilation system implementation of the preferred embodiments of the present invention.

FIG. 6 is a schematic illustration of an alternative ventilation system implementation of the preferred embodiments of the present invention. Using the device 80 of FIG. 5 as an example, collection from a ventilated patient may be facilitated by adding a vacuum system 92 to the outlet 36 of the device 80 and connecting a Y- or T-fitting 94 to the luer lock fitting, described previously, on the end of the nozzle 39. The Y- or T-fitting 94 is connected inline in the middle of the outflow path from the patient 96 to a conventional ventilator 98. The outflow path includes two polyethylene tubes 102, 104, the first of which is connected from a conventional endotracheal tube 100, or other patient interface, to the inlet of the Y- or T-fitting 94, and the second of which is connected between the outlet of the Y- or T-fitting 94 and a port such as the one usually provided on the outflow track of the ventilator 110. A third polyethylene tube 106, is connected from the inflow track of the ventilator 110 to the endotracheal tube 100. Each polyethylene tube 102, 104, 106 may be of approximately 10-30 mm internal diameter and 1 meter or more in length. Together, such an apparatus allows the vacuum system 92 to withdraw a continuous sidestream sample of exhaled breath through the collection device 80 until a sufficient volume of EBC is collected. The rate of aspiration by the pump of the vacuum system 92 may be set at approximately 100 mL/min.

Figure 8:
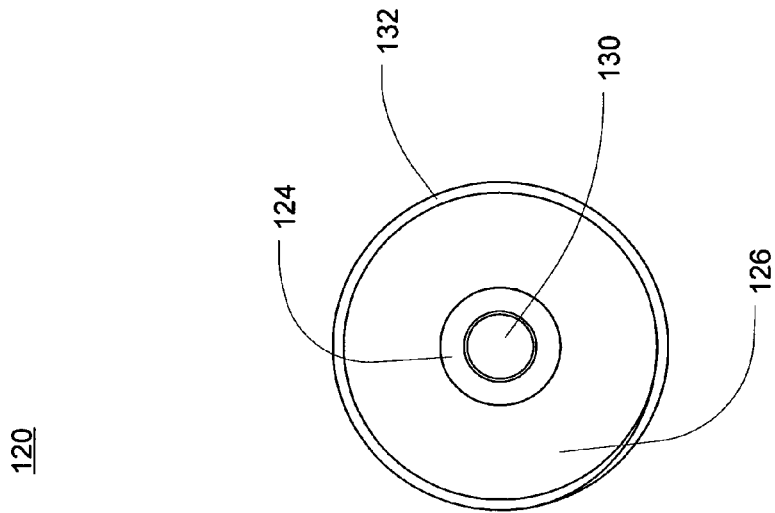
FIG. 8 is a top view of the reaction chamber device of FIG. 7.
Figure 7:
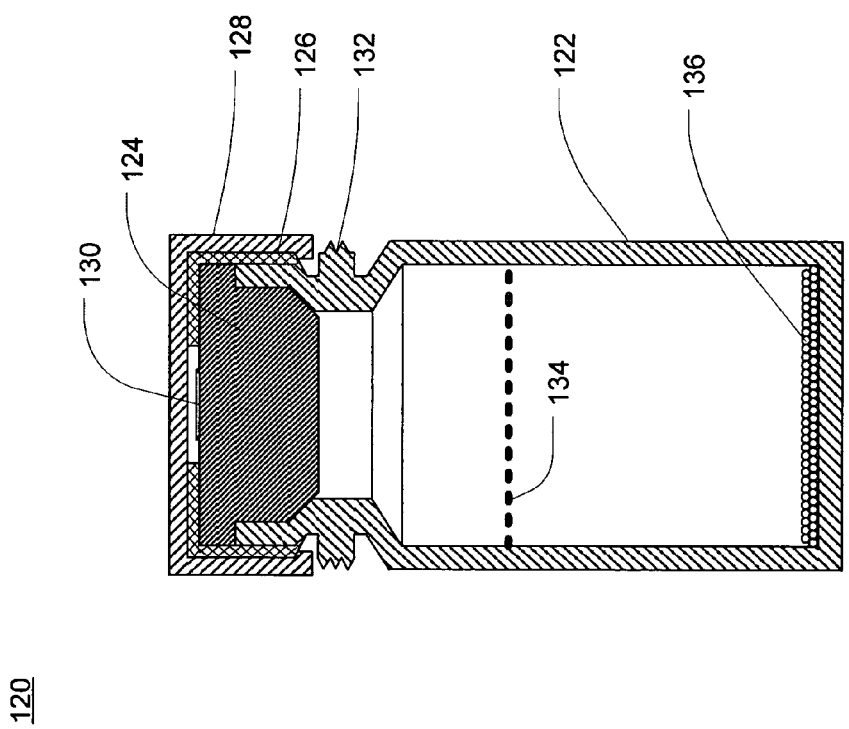
FIG. 7 is a side cross-sectional schematic view of a reaction chamber device suitable for use with the collection devices of FIGS. 2, 4 and 5.

FIGS. 7 and 8 are a side cross-sectional schematic view and a top view, respectively, of one reaction chamber assembly 120 suitable for use with the collection devices 10, 60, 80 of FIGS. 2, 4 and 5. The reaction chamber assembly 120 is designed to detect and quantify the amount of LPS present in the EBC. The assembly 120 resembles the general configuration of a sterile ampule that is commonly used to store drugs for injection. The assembly 120 may function both as a reaction chamber and a spectrophotometer cuvette to measure the percentage of transmission of visible light, which is proportional to the concentration of LPS in the sample. The assembly 120 is vacuum-sealed and includes a reaction chamber 122 and a plug 124, a retaining ring 126, and a protective cap 128. The reaction chamber 122 is preferably made of glass or another transparent material, but may alternatively be made of a semi-transparent (translucent or other non-opaque) material if the chosen color or light change or phenomenon, described below, may be readily seen therethrough. The reaction chamber 122 preferably has a volume of approximately 0.5-1.0 mL. Although as shown the reaction chamber 122 is round, it will be apparent that the reaction chamber 122 can likewise be square or have another geometric shape to facilitate its insertion into a spectrophotometer, or can be altered to allow "retrofitting" into existing commercial laboratory assay systems. The reaction chamber 122 further includes a threaded male luer lock fitting 132 of similar size to that of the condensate collection devices 10, 80 described above. Of course, if a device 60 such as that disclosed in FIG. 4 is utilized, then the luer lock fitting 132 may not be necessary.

The plug 124, which is preferably formed from rubber, may be disposed in the top of the chamber 122 to maintain a sealed, sterile, pyrogen-free environment inside the chamber 122. The plug 124 is retained in the chamber 122 by the retaining ring 126, which is preferably formed from aluminum and has an opening in the center to permit delivery of exhaled breath condensate into the reaction chamber 122 via a delivery port 130 in the plug 124. In a preferred embodiment, the delivery port 130 is a re-sealable cover that may be punctured with a hypodermic needle. The protective cap 128, which is preferably formed from plastic, is temporarily attached over the top of the assembly 120 to protect the retaining ring 126 and plug 124 from damage or soiling.

In use, a sterile reaction chamber assembly 120 is retrieved from storage, and an EBC sample is collected using one of the disclosed devices 10, 60, 80 (or another equivalent device). The protective cap 128 of the reaction chamber assembly 120 is removed and a relatively precise volume of the EBC sample is then delivered to the reaction chamber 122 by inserting the respective hypodermic needle 35 in the delivery port 130 of the plug 124. If provided, the respective luer lock fittings may be engaged, effectively locking the device 10, 60, 80 to the reaction chamber assembly 120. The plunger assembly 25 may then be depressed until a sufficient volume of EBC is delivered to the assembly 120. A calibration line 134 may be marked on the reaction chamber 122 to indicate the necessary volume, but if the volume has been pre-calibrated in the collection device 60, then such a line 134 may not be necessary. During assembly, the reaction chamber 122 may sealed under a vacuum to withdraw a sufficient volume of EBC as needed for accurate measurement of endotoxin analyte.

The chamber 122 contains a prespecified dry mass 136 of factor C, factor B, proclotting enzyme and chromogenic substrate, together with salts of calcium and magnesium, and phosphate salts, or other organic compound, such as TRIS aminomethane buffer to maintain a pH of approximately 7.4 upon hydration. The amounts and activities of these enzymes are precalibrated to allow detection of a clinically relevant range of LPS in the specified volume of EBC. The amounts will be calibrated to allow the reaction to produce a linear optical density reading that ranges from 0 to 1.00 when measured at 15-30 minutes reaction time at approximately 37° C., corresponding proportionately to a concentration of LPS ranging from 0 to approximately 10 EU/mL in undiluted EBC. It is preferred that the temperature of the reaction be held at least about 34° C. It is more preferred that the temperature of the reaction be held at least about 37° C.

The chromogenic substrate can tolerate temperatures up to about 43° C. without loss of activity. As such, the reaction chamber may be heated by a controlled exothermic reaction up to about 43° C. It is preferred that the exothermic reaction be controlled in order to produce even incubation at 34-43° C. for at least 15 minutes, and preferably 25 minutes. Accordingly, and as described hereinbelow, steps should be taken to control the rate of the exothermic hydration reaction.

Such an exothermic reaction may be initiated by placing a salt that liberates heat upon hydration within the reaction chamber. An example of such a salt includes, but is not limited to, sodium thiosulfate pentahydrate. Placing the salt within the reaction chamber allows introduction of the sampled condensate to initiate the exothermic reaction. It is preferred to use a powdered salt, which would facilitate immediate and complete hydration within a short heating period. For example, the salt may be in a semi-permiable matrix or a crystalline form that allows controlled hydration to produce a reaction temperature of 34-43° C. for at least 15 minutes. Alternatively, the salt may be disposed in a user-initiated heating jacket that surrounds the reaction chamber. In this embodiment, the reaction chamber may be inserted into a double-walled jacket consisting of a flexible polymer. The jacket may contain dry salt capable of liberating heat upon hydration and an ampule of water (2-5 mL) that can easily be ruptured by squeezing with two fingers. The action of rupturing the ampule of water initiates hydration of the salt, causing an exothermic reaction, thus heating the reaction chamber to about 43° C. for approximately 15-30 minutes, at which point, the color intensity and corresponding endotoxin activity can be quantified as further described herein below.

Preliminary data suggest that concentrations of LPS exceeding approximately 0.20 EU/mL (a calibrated linear optical density reading of approximately 0.20) will correspond to the clinical test positive threshold, indicating the presence of Gram negative bacterial infection in the lungs. In the preferred embodiment, the chromogenic substrate may be a peptide conjugated to a dye such as para aminoanilde that is cleaved by the clotting enzyme to liberate a yellow color to the reaction solution with peak absorbance at about 405 nm. It should be readily understood that other chromogenic substrates could be substituted, and other dye markers could be conjugated to the substrate which can be detected at different isobestic points. Additionally, the marker molecule may be a compound that contains the property of excitation fluorescence, whereby the molecule liberates light within a narrow wavelength interval in response to stimulation by an incident beam of monochromatic light. One of ordinary skill in the art will understand that various chromogenic and fluorogenic substrates may be used as markers for detecting the presence of the LPS.

Figure 9:
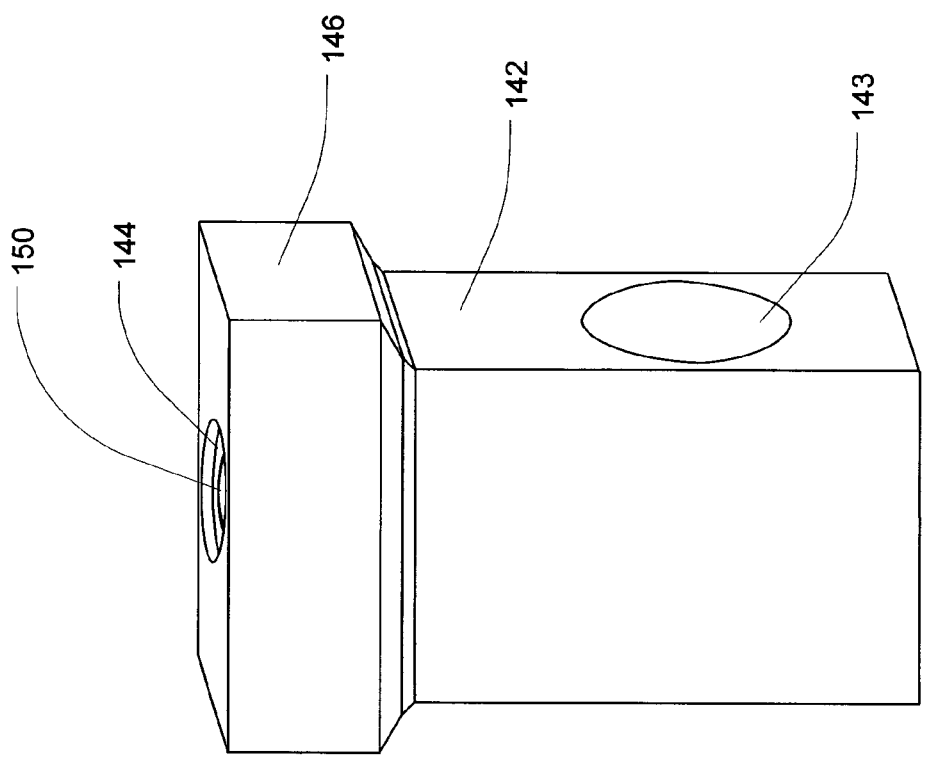
FIG. 9 is a side perspective view of a first alternative reaction chamber device.

Alternatively, a reaction chamber assembly may be designed to capture LPS using antibodies matrix-bound on the sides of the well. FIG. 9 is a perspective view of a first alternative reaction chamber assembly 140. In this alternative embodiment, the assembly 140 would function as a vertical microtiter well employing enzyme-linked immunoassay technology and would have the advantage of allowing detection of species-specific LPS molecules 154. The assembly 140, which may function as a cuvette, may include a chamber 142, a plug 144 and a retaining ring or other structure 146. Windows 143 are formed in at least a portion of the walls of the chamber 142 for a purpose made evident hereinbelow. Like the ring 126 of the previous device 120, the ring 146 includes an opening that exposes an injection target area 150 in the center of the plug 144.

FIGS. 10A-10D are partially schematic, fragmentary side cross-sectional views of the first alternative reaction chamber assembly 140 of FIG. 9. The Fc portion of each antibody 152 is conjugated or bound to the windows 143 of the assembly 140 using conventional techniques. The Fab portion of each antibody 152 is thus oriented toward the center of the assembly 140 to better capture the O-polysaccharide portion of the LPS 154. After introduction of the EBC sample, the chamber 142 may then be washed with an albumin-containing buffer (not shown) to remove nonspecific materials. Then, a separate ampule, containing a prespecified amount of chromogenic substrates 156, such as those described previously, is reconstituted by adding LPS-free water (not shown), and the chromogenic reagent sample is withdrawn by syringe and injected into the reaction chamber 142, as shown in FIG. 10C. The chromogenic substrates 156 react with the LPS 154, thereby liberating a dye 158. After approximately 15-30 minutes, optical density may be read by one of several methods. One chromogenic substrate 156 suitable for use in the preferred embodiments of the present invention incorporates para nitroanilide, which when freed can be detected at about 405-410 nm.

It will be apparent to those of ordinary skill in the art that rather than an antibody with specific immunogenicity toward O-antigen, other molecules with specific and high affinity for any portion of LPS may be bound to the walls of the reaction chamber for capture of LPS. These molecules include, but are not limited to, HA-1A and E5, lipopolysaccharide binding protein ("LPB"), bacteriocidal/permeability increasing protein ("BPI"); limulus anti-lipopolysaccharide factor ("LALF") or the polymyxin antibiotics.

In order to quantify LPS concentration, a number of embodiments may be utilized. In one embodiment, a semi-quantitative determination may be made using a visual comparison to a color strip. The color strip may resemble a standard ruler having patches of one color displayed left to right in incrementally increasing degrees of shade intensity, with the lightest shade being located furthest left and the darkest shade being located furthest right. Each shade patch is associated with a specific range of endotoxin unit (EU) reactivity with increasing degrees of shade intensity signifying increasing EU reactivity. An observer may hold the clear reaction chamber assembly 120, 140 in ambient light next to the plastic or paper color strip for comparing the shade of the contents of the reaction chamber assembly 120, 140 with the color strip patches. The observer may then select the color patch that best matches the color shade intensity observed in the reaction chamber. A positive reaction would be indicated by a specific color shade threshold, corresponding to approximately 0.20 EU/mL or as determined from additional experiments.

More precise quantification may be obtained with a small, specially designed single beam light spectrophotometer that is configured to accept the reaction chamber after incubation as described above. The spectrophotometer may contain a heating coil that is activated upon insertion of the reaction chamber to warm the sample to 37° F. The spectrophotometer may alternatively display or print the measure optical density after 25 minutes of incubation.

Figure 11:
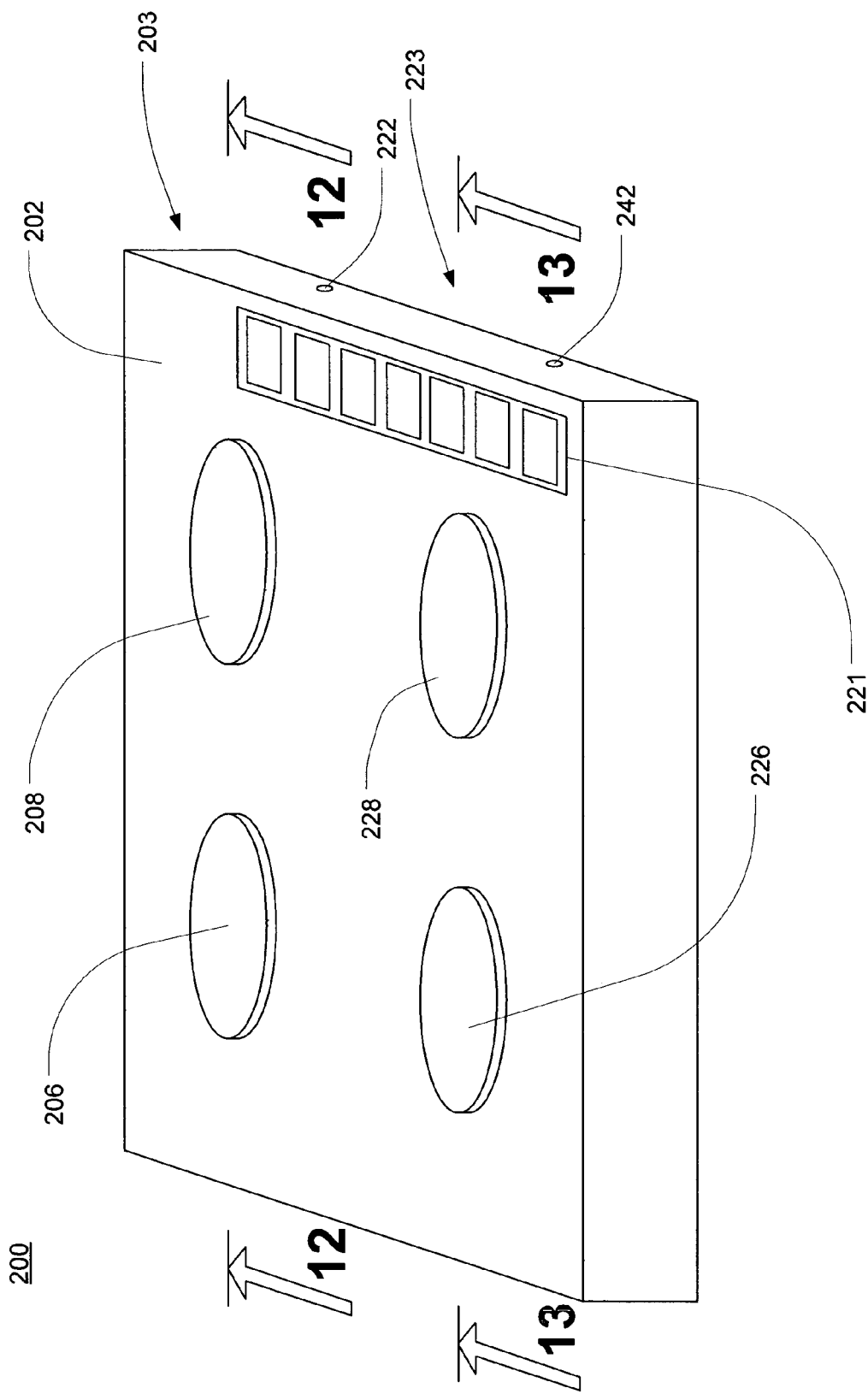
FIG. 11 is a perspective view of a test kit incorporating a second alternative reaction chamber device.

FIG. 11 is a perspective view of a test kit 200 incorporating a second alternative reaction chamber device, which would allow EBC to be delivered to a single-use cartridge that could be read visually without the use of a spectrophotometer. The test kit 200 has two modules 203, 223, including a test module 203 and a positive control module 223, arranged in a housing 202. FIG. 12 is a side cross-sectional view of the test module 203 of FIG. 11, taken along line 12-12. The test module 203 includes a port 204. Port 204 preferably has a volume of approximately 100 microliters and contains dry mass 136 of factor C, factor B, proclotting enzyme and chromogenic substrate, together with EDTA, salts of calcium and magnesium, and phosphate salts, or other organic compound, which allows the dry mass to maintain a pH of approximately 7.4 upon hydration and to form an aqueous reagent.

FIG. 11 further shows a reaction chamber 208, a test matrix 212, a pair of microtubules 214, 216, a pair of one-way valves 218, 220 and an outlet 222. Reaction chamber 208 preferably has a volume of at least about 250 microliters. The port 204 and reaction chamber 208 are connected by the first microtubule 214, while the reaction chamber 208 is connected to the outlet 222 by the second microtubule 216. One of ordinary skill in the art will understand that microtubule 214 may include one or more microtubules. Valves 218, 220 are disposed in the first and second microtubules 214, 216, respectively, so as to facilitate one-way fluid communication from the port 204 through the reaction chamber 208 to the outlet 222. If microtubule 214 includes a plurality of microtubules, more than one valve 218, 220 may be necessary to accommodate the plurality of microtubules. The top of the cartridge has a preprinted color strip 221 with a series of successively darker color patches disposed thereon and arranged such that each successively darker color patch corresponds to an incrementally greater interval of endotoxin activity.

The chamber 208 is covered with a clear material 210 to allow viewing of the matrix 212 for color change indicating the presence of LPS. The matrix 212, which is arranged in the chamber 208, is a surface formed from an insoluble polymer or other material that will accept and be stained by the chromogenic substrate. Suitable materials include, but are not limited to, polymers derived from cellulose, agarose, methacrylate, polystyrene, polyphenyl, polynaphthyl, polybenzyl, nylon, silk or other fabric and the like. The matrix 212 is absorbent but tightly woven such that it permits fluid to remain suspended in the chamber 208 until the fluid moves by gravity and capillary action through microtubule 216. As an advantage, the matrix 212 may intrinsically bind LPS itself or may covalently or otherwise bind one of the LPS-binding molecules, such as HA-1A and E5, LPB, BPI, LALF or the polymyxin antibiotics. The matrix 212, therefore, develops a color intensity in proportion to the concentration of endotoxin in the unknown sample. Visual comparison to the pre-printed color-strip 221 allows a semi-quantitative determination of endotoxin concentration, as described above.

The interior of the test kit 200 may also contain sodium thiosulfate pentahydrate and a sealed ampule of water that ruptures upon squeezing of the test kit 200. The action of rupturing the ampule of water will initiate hydration of the sodium thiosulfate, causing an exothermic reaction, thus heating the entire test kit 200 to about 43° C. for approximately 25 minutes. Although the materials for the exothermic reaction are disposed within the test kit 200, they are separated from all areas of the test kit 200 in which the sample is introduced and in which any LPS-related chemical reactions occur.

In operation, the reaction is initiated by injecting condensate collected with device 10, 60, 80 into the chamber 204 that contains the dry mass 136 described previously. It is preferred that at least about 0.35 mL of condensate be injected into the reaction chamber 204. The action of injecting the condensate causes a mixing action of the condensate and dry mass 136 in the reaction chamber 204 and the microtubule 214, thereby initiating the LAL reaction. The pressure differential induced by injection, coupled with the force of capillary action causes the reaction mixture to flow down microtubule 214 into the reaction chamber 208, where it remains while the chromogenic reaction continues at a temperature of 34-43° C. Since endotoxin will be bound to the matrix 212, the colored molecule that is hydrolyzed from the chromogenic substrate will stain the matrix 212 in a color hue intensity that is proportional to the activity of endotoxin in the condensate, the color change can be visually compared with the color strip 221 for quantitation.

FIG. 13 is a side cross-sectional view of the positive control module 223 of FIG. 11, taken along line 13-13. The positive control module 223 includes a port 224; a reaction chamber 228; a test matrix 232; a quantity of dry LPS combined with dry mass 136, represented herein as 244; a pair of microtubules 234, 236; a pair of one-way valves 238, 240 and an outlet 242. The port 224 and reaction chamber 228 are connected by the first microtubule 234, and the reaction chamber 228 is connected to the outlet 242 by the second microtubule 236. The valves 238, 240 are disposed in the first and second microtubules 234, 236, respectively, so as to permit one-way fluid communication from the port 224 through the reaction chamber 228 to the outlet 242. As illustrated, the LPS 244 is disposed in the port 224, but it will be apparent that the LPS 244 may alternatively or additionally be disposed in the first microtubule 234 or on the test matrix 232.

The second alternative reaction chamber device may also be used as follows. An EBC sample is injected from one of the previously-described breath condensate collection devicees 10, 60, 80 into the test module port 204, from where it may be directed via the first test module microtubule 214 to the test module reaction chamber 208. In a preferred embodiment, the volume of the EBC sample is about 0.35 mL. The volume of the sample is preferably calibrated such that the well 208 containing the matrix 212 fills to capacity, thus covering the matrix 212 with liquid and initiating LPS binding to the matrix 212. Excess EBC may flow out through the second test module microtubule 216. The one-way valve 218 prevents entry of LPS from ambient air. Absorbent material may be placed in 216 to prevent any external fluid leak.

After a relatively precise predetermined period of time, which may be about 60 seconds, the test module 203 and the positive control module 223 may each be washed with a quantity of sterile (endotoxin-free) water. In a preferred embodiment, the volume of sterile water that is injected into each module 203, 223 is about 0.25 mL. The water passes through the respective reaction chambers 208, 228 and is allowed to drain through the respective outlets 222, 242 via the respective second microtubule 216, 236.

Next, LPS-free water is added to an ampule, such as the reaction chamber device 120 of FIGS. 7 and 8, containing a dry mass 136 of factor C, factor B, proclotting enzyme and chromogenic substrate, together with EDTA, salts of calcium and magnesium, and phosphate salts, or other organic compound to maintain a pH of approximately 7.4 upon hydration to form an aqueous reagent. Once the reagent is reconstituted, it may be withdrawn using a syringe such as that commonly used to deliver insulin or to provide tuberculosis testing antigen (often referred to as a "TB syringe") (not shown) and injected into both the test module port 204 and the positive control module port 224. The test kit 200 may then be left to develop for a prespecified time interval, e.g., 10 minutes at 23° C., and then visually inspected for color or pattern change in the test well 208. The positive control module 223 is included to ensure activity of the chromogenic enzyme system.

In a still further alternative, the proportion of LPS in EBC could be measured by allowing gel formation of the clotting cascade within a narrow tube, as described in Neeman et al., U.S. Pat. No. 4,370,413, (the '413 patent), the entirety of which is incorporated herein by reference. FIG. 14 is a partial side cross-sectional view of a breath condensate collection device 260 in accordance with a fourth preferred embodiment of the present invention. This device 260 is similar to that of FIG. 4, in that it includes a syringe 262 having double walls 22, 32, a central chamber 24, a plunger assembly 65 with a piston 26, a rubber gasket 28 and a handle 30, a breath input assembly (not shown), an outlet 68, a threaded nozzle 61, and a removable plastic covering 69. Each of these components is generally similar to those of the device 60 of FIG. 4, except that the syringe 262 further includes a manometer 265 extending from the side of the syringe in fluid communication with the outlet 68. In addition, although each device 60, 260 includes a needle 35, 275, the needle 275 of this fourth embodiment serves as the narrow tube in which EBC is contacted with the LAL assay reagent. Accordingly, the needle 275 is plugged with a dry, insoluble and inert fiber matrix 270, as shown in FIG. 15, which is preloaded with the LAL assay reagent for gelation if LPS is present in the EBC.

A reaction may be initiated by depressing the plunger assembly 65 until the plug 270 is wetted with EBC. The amount of gelation in the outflow needle 275 will be proportional to the amount of LPS in the EBC. After a specified period of time, the plunger assembly 65 may be forcibly depressed again, and the extrusion pressure measured within the central chamber 24 using the manometer 265. The extrusion pressure is proportional to the LPS concentration in the EBC.

In all of the preceding embodiments, it should be recognized that the specificity of the reaction can be enhanced by inclusion of chemicals or methods to prevent reaction with beta glucans (factor G), including heating the sample to 75° C., adding alkylglucosides, or molecules with beta 1,4 glucosidic linkages.

Once a Gram negative bacterial infection is diagnosed, antibiotic therapy may begin. Those skilled in the art will understand that the method of the present invention may be utilized to monitor the effectiveness of antibiotic therapy. It can be predicted by those skilled in the art, that effective antibiotic therapy may cause an initial increase in LPS concentration in expired breath condensate, owing to bacterial demise with cell membrane rupture and increased release of free LPS into alveolar epithelial fluid. This concentration increase would be expected in the first 24 to 72 hours after antibiotic administration. It could further be predicted that effective antibiotic therapy would eventually cause a decrease in the concentration of LPS in expired breath condensate over the subsequent 3-10 days after antibiotic administration. Accordingly, it can be surmised that serial LPS measurements may be used to monitor treatment efficacy. A failure to exhibit an initial increase in expired LPS content or a failure to exhibit a decline in expired LPS content in the subsequent days could signal resistance of the Gram negative bacteria to treatment.

The present invention is advantageous because it provides a method and device for diagnosing a Gram negative bacterial infection in a relatively easy, painless and quick manner. The present application is directed to diagnosing Gram negative bacterial pneumonia by measuring the concentration of LPS in exhaled breath condensate. However, the present invention may also be utilized to diagnose any intrapulmonary Gram negative bacterial infection, including, but not limited to, septicemia. One of ordinary skill in the art will understand that Gram negative bacterial infections may be treated with the same antibiotic treatment and thus diagnoses of any Gram negative bacterial infection is beneficial for a subject suffering from such infection. Further, the present invention may also be utilized to identify a specific strain of Gram negative bacteria causing infection in a situation in which this information may be beneficial.

EXAMPLES

Example 1

LPS was detected in exhaled breath condensate samples from subjects that were awake, cooperative and able to breathe spontaneously in order to diagnose whether such subjects had Gram negative bacterial pneumonia according to the following procedure.

The subjects for the procedure were selected according to the following procedure. Subjects (N=8 per group) were recruited based upon three criteria: 1) diagnosis of pneumonia, 2) healthy patients who actively smoked more than 10 cigarettes per day and 3) healthy nonsmokers. To obtain subjects diagnosed with pneumonia, subjects diagnosed on standard clinical grounds, including cough productive of colored sputum, measured fever >101° F., a leukocytosis, evidenced by a peripheral total white blood count of >12,000 cells per cubic microliter, and the presence of an infiltrate on chest radiograph were selected. Exclusion criteria for subjects included any use of antimicrobial medications, acute illness or anatomical abnormality that precluded breath collection and/or suspected pulmonary tuberculosis.

The breath condensing device utilized for collected exhaled breath samples is described as follows. The device consisted of a one-meter long polyvinyl tube (15 mm ID) attached to a modified glass flask, which was approximately 50 cm in height. The glass flask had a specially designed, removable glass stopper at the top but was otherwise similar in appearance to a standard laboratory volumetric (Florence) flask. The glass stopper had two ports, one for entry of a glass tube that projected upward and was bent at a 90° angle and another to allow dried, exhaled air to exit into ambient air. One end of the glass tube was connected to a polyvinyl tube that fit snugly over the glass tube. The other end of the glass tube projected into the interior of the glass bulb of the flask by approximately 25 cm. The entire glass flask was submerged in a cooling slurry of frozen carbon dioxide in ethanol.

Exhaled breath condensate was collected according to the following procedure. A subject was allowed to hold the polyvinyl tube and breath into a duckbill-shaped mouthpiece that was attached to the opposite end of the polyvinyl tube. The subject's breath passed through the polyvinyl tube into the condenser chamber of the flask, where the cooled inner side of the flask would condense and freeze the expired water vapor and aerosolized droplets in the subject's breath. Subjects were asked to deliver approximately 30 deep exhalations, which yielded approximately 1-3 mL of sample.

Prior to collection of breath samples from subjects, multiple steps were take to reduce sample contamination with extraneous endotoxin or beta glucan molecules. All components were sterilized by autoclaving at 220° C. for a minimum of 4 hours between uses and by using a commercially available washing solution designed to remove endotoxin. The polyvinyl tube was wrapped in sterile foil prior to autoclaving. The sterile foil was left in place during sample collection but was removed prior to removing the polyvinyl tube. The technician used sterile gloves to handle all components. However, the terminal 6 cm of the polyvinyl tube was able to be grasped by the subject, who did not wear sterile gloves. After the condensate was allowed to melt, it was aspirated from the condenser chamber with pyrogen-free pipette tips and transferred to pyrogen-free cryotubes under a laminar hood. To examine for background endotoxin, a "mock" standard of the glassware and tubing was conducted according to the following procedure. Two milliliters of endotoxin-free water (Sigma Chemical, St. Louis, Mo.) was instilled into the washed, autoclaved condenser chamber, agitated and then aspirated and stored in the same manner as the condensate samples. Condensate samples and the water run for a mock standard were stored at −57° C. until assay.

The presence of endotoxin was detected according to the following procedure. An assay was performed on undiluted, thawed condensate using a chromogenic limulus assay according to manufacturer's specifications (Pyrochrome Assay, Associates of Cape Cod, Falmouth, Mass., USA). Reactions were carried out on 96-well microtitre plates (Pyrochrome microtitre plates, Associates of Cape Cod) at 37° C. for 30 min, and the color change read with a microtitre plate spectrophotometer at 405 nm. All samples were run during one batch. The standard curve was performed using the assay endotoxin standard and was linear with R=0.997.

Figure 16:
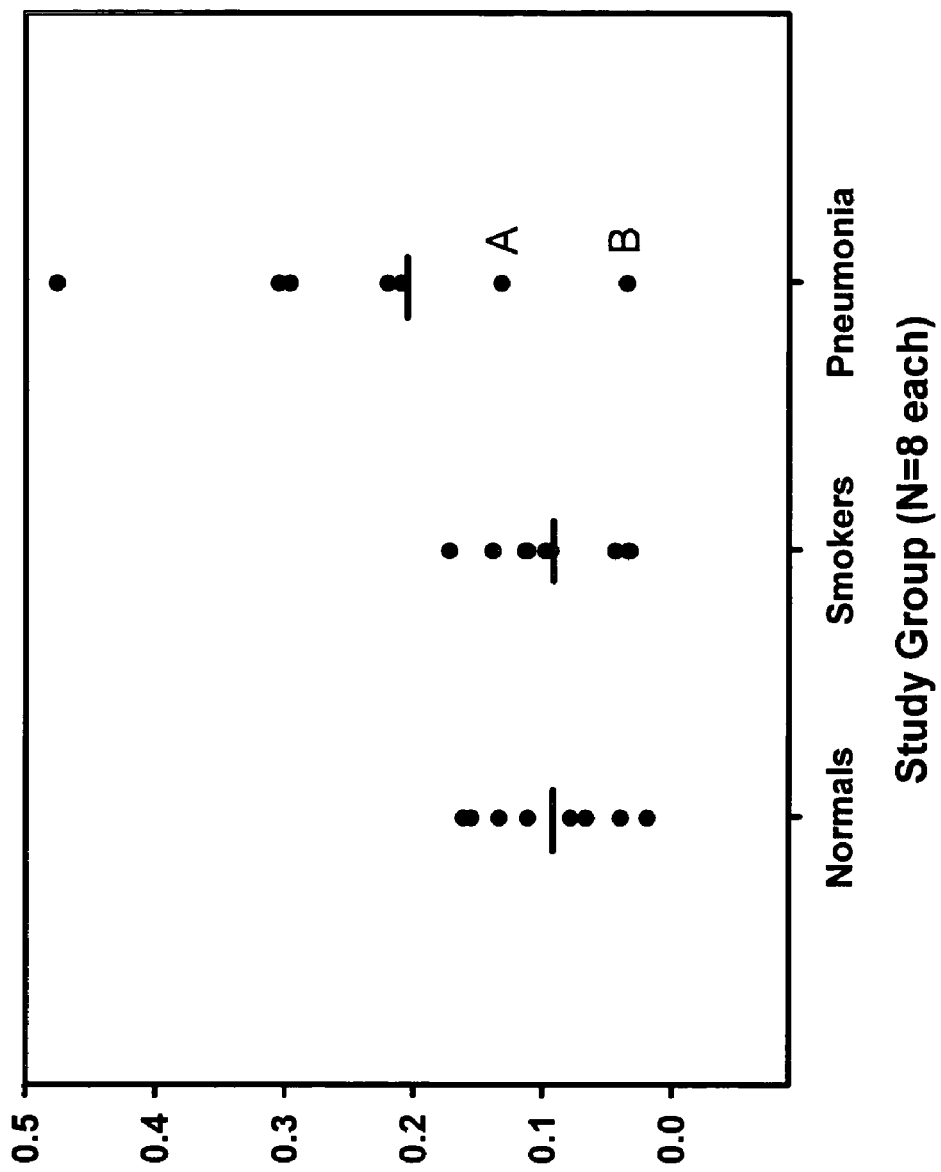
FIG. 16 is a scatter plot graph illustrating the measured endotoxin concentrations for patients in each of three study groups.

FIG. 16 is a scatter plot graph illustrating the measured endotoxin concentrations for patients in each of three study groups. The mean (±SD) endotoxin concentration in normals, smokers, and patients with pneumonia was 0.096±0.050, 0.091±0.040, and 0.234±0.130 EU/mL, respectively. The plot suggests that 0.20 EU/mL may be a useful cutoff point to distinguish subjects with Gram negative pneumonia from subjects without Gram negative pneumonia.

Two subjects with pneumonia and test values below 0.20 EU/mL are labeled "A" and "B". Traditional clinical tests confirmed that these subjects did not have Gram negative bacterial pneumonia. Patient A had blood cultures that were positive for *streptococcus pneumonia*, which was clinically presumed to be the bacterial cause of the patient's pneumonia; patient B had clinically suspected influenzal (viral) pneumonia with negative blood cultures and no other specimens submitted for analysis.

Two of the water samples from the mock standard had values of 0.10 and 0.14 EU/mL (mean 0.12 EU/mL). Accordingly, 0.12 EU/mL was considered the background "noise" of the system, and this value was subtracted from the cutoff value of 0.20 EU/mL determined in uncorrected samples. Using this analysis, a sample of expired breath condensate containing a value above 0.08 EU/mL would be considered an abnormal test result. It should be recognized that this background correction value may differ if a different condenser apparatus is used in another laboratory.

Example 2

LPS was detected in exhaled breath condensate samples from subjects that were breathing with the assistance of a ventilator in order to diagnose whether such subjects had Gram negative bacterial pneumonia according to the following procedure.

Six subjects participated in the study. Four of the ventilated subjects presented clinical evidence of pneumonia and were being treated with antibiotic therapy, and two of the ventilated subjects presented no clinical evidence of pneumonia and were used as controls.

Breath condensate samples were obtained according to the following procedure. The analyte was obtained from the exhaled breath condensate that accumulated in outflow tubing attached to the endotracheal tube of the ventilation system. Analyte appeared clear and non-turbid upon visual inspection.

The presence of endotoxin was detected according to the following procedure. An assay was performed on undiluted and diluted condensate using a chromogenic limulus assay according to manufacturer's specifications (Pyrochrome Assay, Associates of Cape Cod, Falmouth, Mass., USA). The dilutions included 1:10, 1:100 and 1:1000 dilutions in endotoxin-free water. Reactions were carried out on 96-well microtitre plates (Pyrochrome microtitre plates, Associates of Cape Cod) at 37° C. for 30 minutes, and the color change read with a microtitre plate spectrophotometer at 405 nm. All samples were run during one batch. The upper limit of detection of the assay was 0.25 EU/mL.

The results of the assay are as follows. All six samples were above limits of detection in the undiluted samples (i.e., greater than 0.25 EU/mL). The mean endotoxin concentration in all the 1:10 dilution samples of subjects with pneumonia was above the limit of linear detection, but the mean endotoxin concentration from the two ventilated patients without pneumonia in the 1:10 dilutions was <0.05 EU/mL. These data suggest that the presence of more than 0.25 EU/mL in samples of condensate in the outflow tubing of a ventilator circuit that appear clear and non-turbid upon visual inspection would predict the presence of a bronchoalveolar lavage sample that would be positive for gram negative pneumonia.

Example 3

LPS was detected in exhaled breath condensate according to the following procedure. A commercially available 1-liter volume glass flask was prepared for collecting breath condensate samples according to the following procedure. The glass was heated to 400° C. for 3 hours to render its surfaces LPS-free. A sterilized, flexible polyvinyl tube, 11 mm in internal diameter, was arranged in fluid communication to a side-arm of the flask such that when a patient breathed into the tube, the patient's breath passed through the glass flask and out through an exit port. The flask was partially submerged in a dry ice and ethanol slurry mixture as a coolant to facilitate capture of exhaled breath condensate in the flask. The tube and flask were arranged in a fashion to keep the condensing flask above the level of the patient to prevent any capture of aerosolized saliva.

Exhaled breath was collected according to the following procedure. Eight subjects of varying health status breathed into the tube connected to the flask. Each subject breathed 100 deep exhalations into the flask, using a hand counter to keep track of breaths. This method provided a mean volume of condensate equal to 11±4 mL.

A chromogenic commercial LAL assay (Cape Cod, Mass.) was used to detect LPS in the exhaled breath condensate according to the following procedure. From each subject's condensate sample, duplicate 50 µL aliquots were transferred into two wells of a standard 96-well ELISA plate. The reagents required for the chromogenic LAL assay were added and the samples were incubated for 30 minutes at 37° C. The optical density was read at 405 nm in a commercially available plate well reader. Concentrations were determined by comparison to a standard curve using known amounts of LPS obtained from a FDA-certified source.

Results were obtained as follows. Four normal volunteers were all found to have concentrations of LPS below 100 pg/mL, whereas two otherwise healthy smokers were found to have concentrations below 200 pg/mL. Two smokers with clinical pneumonia were found to have EBC LPS concentrations above 800 pg/mL. From this experiment, it was concluded that LPS content of EBC samples can vary based upon the health of the lung in the subjects providing the samples. These data also suggest that EBC can be sampled without contamination from oral flora in healthy subjects.

Based on the foregoing information, it is readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to its preferred embodiment, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof. Although specific terms are employed herein, they are used in a generic and descriptive sense only and not for the purpose of limitation.

What is claimed is:

1. A method for diagnosing and monitoring intrapulmonary Gram negative bacterial infection in an air-breathing vertebrate subject, comprising:
   (a) collecting exhaled breath condensate from an air-breathing vertebrate subject;
   (b) providing a reaction chamber with an interior surface, wherein said reaction chamber has a material that binds lipopolysaccharide disposed therein;
   (c) delivering at least a portion of the collected breath condensate to the reaction chamber;
   (d) washing the reaction chamber with a buffer;
   (e) delivering a reaction reagent to the reaction chamber;
   (f) determining whether the subject has an intrapulmonary Gram negative bacterial infection based on a physical change that occurs when the at least a portion of the collected exhaled breath condensate is delivered to the reaction chamber, wherein said physical change is caused by the presence of lipopolysaccharide in the exhaled breath condensate, and
   (g) identifying the particular strain of the intrapulmonary Gram negative bacteria;
   wherein identifying includes identifying the particular strain of intrapulmonary Gram negative bacteria based upon a determination of the O-antigen portion of the lipopolysaccharide molecule,
      wherein the binding material is embedded in a matrix surface disposed within the reaction chamber.

2. A method for diagnosing and monitoring intrapulmonary Gram negative bacterial infection in an air-breathing vertebrate subject, comprising:
   collecting exhaled breath condensate from the air-breathing vertebrate subject;
   providing a reaction chamber, wherein said reaction chamber has a reaction reagent disposed therein;
   delivering at least a portion of the collected exhaled breath condensate to the reaction chamber;
   determining whether the subject has an intrapulmonary Gram negative bacterial infection based on a physical change that occurs when at least a portion of the collected exhaled breath condensate is delivered to the reaction chamber, wherein said physical change is caused by the presence of lipopolysaccharide in the exhaled breath condensate; and
   identifying the particular strain of the intrapulmonary Gram negative bacteria;
wherein identifying includes identifying the particular strain of intrapulmonary Gram negative bacteria based upon a determination of the O-antigen portion of the lipopolysaccharide molecule.

3. A method for diagnosing and monitoring intrapulmonary Gram negative bacterial infection in an air-breathing vertebrate subject, comprising:

- collecting exhaled breath condensate from an air-breathing vertebrate subject;
- providing a reaction chamber, wherein said reaction chamber has a reaction reagent disposed therein;
- delivering at least a portion of the collected exhaled breath condensate to the reaction chamber;
- determining whether the subject has an intrapulmonary Gram negative bacterial infection based on a physical change that occurs when the at least a portion of the collected exhaled breath condensate is delivered to the reaction chamber, wherein said physical change is caused by the presence of lipopolysaccharide in the exhaled breath condensate;
- visually matching a color change in the reaction chamber to a standard, wherein said standard comprises a printed strip of color patches of increasing hue intensity, and wherein each color patch corresponds to increasing concentrations of lipopolysaccharide, respectively, and
- identifying the particular strain of the intrapulmonary Gram negative bacteria;

wherein identifying includes identifying the particular strain of intrapulmonary Gram negative bacteria based upon a determination of the O-antigen portion of the lipopolysaccharide molecule.

4. A method for diagnosing and monitoring intrapulmonary Gram negative bacterial infection in an air-breathing vertebrate subject, comprising:

- collecting exhaled breath condensate from an air-breathing vertebrate subject;
- providing a reaction chamber with an interior surface, wherein said reaction chamber contains a material that binds lipopolysaccharide disposed therein;
- delivering at least a portion of the collected breath condensate to the reaction chamber;
- washing the reaction chamber with a buffer;
- delivering a reaction reagent to the reaction chamber; and
- determining whether the subject has an intrapulmonary Gram negative bacterial infection based on a physical change that occurs when the at least a portion of the collected exhaled breath condensate is delivered to the reaction chamber, wherein said physical change is caused by the presence of lipopolysaccharide in the exhaled breath condensate, and
- identifying the particular strain of the intrapulmonary Gram negative bacteria;

wherein identifying includes identifying the particular strain of intrapulmonary Gram negative bacteria based upon a determination of the O-antigen portion of the lipopolysaccharide molecule.

* * * * *